(12) United States Patent
Ruan et al.

(10) Patent No.: US 11,156,960 B2
(45) Date of Patent: Oct. 26, 2021

(54) FOCUSING LIGHT INSIDE SCATTERING MEDIA WITH MAGNETIC PARTICLE GUIDED WAVEFRONT SHAPING

(71) Applicant: California Institute of Technology, Pasadena, CA (US)

(72) Inventors: Haowen Ruan, Pasadena, CA (US); Jacob Berlin, Duarte, CA (US); Tom Haber, Duarte, CA (US); Changhuei Yang, South Pasadena, CA (US)

(73) Assignees: CALIFORNIA INSTITUTE OF TECHNOLOGY, Pasadena, CA (US); CITY OF HOPE, A NON-PROFIT CHARITABLE ORGANIZATION, Duarte, CA (US)

( * ) Notice: Subject to any disclaimer, the term of this patent is extended or adjusted under 35 U.S.C. 154(b) by 356 days.

(21) Appl. No.: 16/058,498

(22) Filed: Aug. 8, 2018

(65) Prior Publication Data
US 2019/0064736 A1    Feb. 28, 2019

Related U.S. Application Data

(60) Provisional application No. 62/542,656, filed on Aug. 8, 2017, provisional application No. 62/564,850, filed on Sep. 28, 2017.

(51) Int. Cl.
*G01N 21/47*   (2006.01)
*G03H 1/04*   (2006.01)
(Continued)

(52) U.S. Cl.
CPC ....... *G03H 1/0443* (2013.01); *G01N 21/4795* (2013.01); *G01N 33/4833* (2013.01);
(Continued)

(58) Field of Classification Search
CPC .. G03H 1/0443; G03H 1/2294; G03H 1/0005; G03H 1/0465; G03H 2001/0083;
(Continued)

(56) References Cited

U.S. PATENT DOCUMENTS

| | | | |
|---|---|---|---|
| 7,747,304 B2* | 6/2010 | Gleich | A61K 49/001 600/407 |
| 10,203,274 B2* | 2/2019 | Ruan | G01N 21/453 |

(Continued)

OTHER PUBLICATIONS

Liu, Y., et al., "Focusing light inside dynamic scattering media with millisecond digital optical phase conjugation", Optica, Feb. 2017, pp. 280-288, vol. 4, No. 2.
(Continued)

*Primary Examiner* — William R Alexander
*Assistant Examiner* — Rahman Abdur
(74) *Attorney, Agent, or Firm* — Gates & Cooper LLP

(57) ABSTRACT

A magnetic field controlled guidestar for focusing light deep inside scattering media using optical phase conjugation. Compared with the optical and ultrasonic field, the magnetic field has an exceptional penetration depth. The magnetic particle guidestar has a high light-tagging efficiency, good biocompatibility, and a small diameter which enables a sharp and bright focusing deep inside biological tissue. This new method can benefit a wide range of biomedical applications including deep-tissue imaging, neural modulation, and targeted photothermal and photodynamic therapies.

20 Claims, 15 Drawing Sheets

(51) Int. Cl.
 G01N 33/483 (2006.01)
 G03H 1/22 (2006.01)
 G03H 1/00 (2006.01)
(52) U.S. Cl.
 CPC ......... *G03H 1/0005* (2013.01); *G03H 1/0465* (2013.01); *G03H 1/2294* (2013.01); *G03H 2001/0083* (2013.01); *G03H 2001/0447* (2013.01); *G03H 2001/0458* (2013.01); *G03H 2001/0471* (2013.01); *G03H 2225/30* (2013.01)
(58) Field of Classification Search
 CPC ....... G03H 2001/0447; G03H 2225/30; G03H 2001/0458; G03H 2001/0471; G01N 33/4833; G01N 21/4795
 USPC .......................................................... 359/11
 See application file for complete search history.

(56) References Cited

U.S. PATENT DOCUMENTS

| | | | | |
|---|---|---|---|---|
| 2007/0184471 | A1* | 8/2007 | Yguerabide | C12Q 1/6834 435/6.1 |
| 2009/0015831 | A1* | 1/2009 | Yguerabide | C12Q 1/6816 356/337 |
| 2015/0241342 | A1* | 8/2015 | Zhou | G01N 15/1425 356/432 |
| 2016/0356695 | A1* | 12/2016 | Gabriel | G01N 15/0211 |

OTHER PUBLICATIONS

Ntziachristos, V., "Going deeper than microscopy: the optical imaging frontier in biology", Nature Methods, Aug. 2010, pp. 603-614, vol. 7, No. 8.
Vellekoop, I.M., et al., "Focusing coherent light through opaque strongly scattering media", Optics Letters, Aug. 15, 2007, pp. 2309-2311, vol. 32, No. 16.
Vellekoop, I.M., "Feedback-based wavefront shaping", Optics Express, Apr. 2015, pp. 12189-12206, vol. 23, No. 9.
Mosk, A.P., et al., "Controlling waves in space and time for imaging and focusing in complex media", Nature Photonics, May 2012, pp. 283-292, vol. 6.
Horstmeyer, R., et al., "Guidestar-assisted wavefront-shaping methods for focusing light into biological tissue", Nature Photonics, Sep. 2015, pp. 563-571, vol. 9.
Yu, H., et al., "Recent advances in wavefront shaping techniques for biomedical applications", Curr. Appl. Phys., 2015, pp. 632-641, vol. 15.
Popoff, S.M., et al., "Measuring the Transmission Matrix in Optics: An Approach to the Study and Control of Light Propagation in Disordered Media", Physical Review Letters, Mar. 2010, pp. 100601-1-100601-4, vol. 104.
Kim, M., et al., "Transmission matrix of a scattering medium and its applications in biophotonics", Opt. Express, 2015, pp. 12648-12668, vol. 23.
Chaigne, T., et al., "Controlling light in scattering media noninvasively using the photo-acoustic transmission-matrix", Nature Photonics, 2014, pp. 58-64, vol. 8.
Yu, H., et al., "Measuring Large Optical Transmission Matrices of Disordered Media", Physical Review Letters, Oct. 2013, pp. 153902-1-153902-5, vol. 111.
Jang, M., et al., "Relation between speckle decorrelation and optical phase conjugation (OPC)-based turbidity suppression through dynamic scattering media: a study on in vivo mouse skin", Biomedical Optics Express, 2015, pp. 72-85, vol. 6, No. 1.
Brake, J., et al., "Analyzing the relationship between decorrelation time and tissue thickness in acute rat brain slices using multispeckle diffusing wave spectroscopy", Journal of the Optical Society of America A, Feb. 2016, pp. 270-275, vol. 33, No. 2.
Liu, Y., et al., "Optical focusing deep inside dynamic scattering media with near-infrared time-reversed ultrasonically encoded (TRUE) light", Nature Communications, 2015, pp. 1-9, vol. 6, No. 5904.
Cui, M., et al., "Implementation of a digital optical phase conjugation system and its application to study the robustness of turbidity suppression by phase conjugation", Optics Express, Feb. 2010, pp. 3444-3455, vol. 18, No. 4.
Hsieh, C., et al., "Digital phase conjugation of second harmonic radiation emitted by nanoparticles in turbid media", Optics Express, Jun. 2010, pp. 12283-12290, vol. 18, No. 12.
Papadopoulos, I.N., et al., "Focusing and scanning light through a multimode optical fiber using digital phase conjugation", Optics Express, May 2012, pp. 10583-10590, vol. 20, No. 10.
Hillman, T.R., et al., "Digital optical phase conjugation for delivering two-dimensional images through turbid media", Scientific Reports, 2013, pp. 1-5, vol. 3, No. 1909.
Lee, K., et al., "One-wave optical phase conjugation mirror by actively coupling arbitrary light fields into a single-mode reflector", Phys. Rev. Lett., Oct. 2015, pp. 1-5, vol. 115, No. 153902.
Ji, N. et al., "Adaptive optics via pupil segmentation for high-resolution imaging in biological tissues", Nature Methods, Feb. 2010, pp. 141-147, vol. 7, No. 2.
Vellekoop, I.M., et al., "Scattered light fluorescence microscopy: imaging through turbid layers", Optics Letters, Apr. 2010, pp. 1245-1247, vol. 35, No. 8.
Kong, F., et al., "Photoacoustic-guided convergence of light through optically diffusive media", Optics Letters, Jun. 2011, pp. 2053-2055, vol. 36, No. 11.
Tzang, O., et al., "Thermal expansion feedback for wave-front shaping", Optics Express, Mar. 2017, pp. 6122-6131, vol. 25, No. 6.
Lai, P., et al., "Photoacoustically guided wavefront shaping for enhanced optical focusing in scattering media", Nature Photonics, Feb. 2015, pp. 126-132, vol. 9.
Jang, J., et al., "Complex wavefront shaping for optimal depth-selective focusing in optical coherence tomography", Optics Express, Feb. 2013, pp. 2890-2902, vol. 21, No. 3.
Xu, X., et al., "Time-reversed ultrasonically encoded optical focusing into scattering media", Nature Photonics, Mar. 2011, pp. 154-157, vol. 5.
Wang, Y.M., et al., "Deep-tissue focal fluorescence imaging with digitally time-reversed ultrasound-encoded light", Nature Communications, 2012, pp. 1-8, vol. 3, No. 928.
Si, K., et al., "Fluorescence imaging beyond the ballistic regime by ultrasound pulse guided digital phase conjugation", Oct. 2012, pp. 657-661, vol. 6.
Ruan, H., et al., "Iterative Time-Reversed Ultrasonically Encoded Light Focusing in Backscattering Mode", Scientific Reports, Nov. 2014, pp. 1-7, vol. 4, No. 7156.
Tay, J.W., et al., "Ultrasonically encoded wavefront shaping for focusing into random media", Scientific Reports, Jan. 2014, pp. 1-5, vol. 4, No. 3918.
Ruan, H., et al., "Optical focusing inside scattering media with time-reversed ultrasound microbubble encoded light", Nature Communications, Nov. 2015, pp. 1-8, vol. 6, No. 8968.
Ma, C., et al., "Time-reversed adapted-perturbation (TRAP) optical focusing onto dynamic objects inside scattering media", Nature Photonics, Dec. 2014, pp. 931-936, vol. 8, No. 12.
Zhou, E.H., et al., "Focusing on moving targets through scattering samples", Optica, Oct. 2014, pp. 227-232, vol. 1, No. 4.
Plouffe, B.D., et al., "Fundamentals and application of magnetic particles in cell isolation and enrichment: a review", Reports on Progress in Physics, 2015, pp. 1-38, vol. 78.
White, E.E., et al., "Functionalized Iron Oxide Nanoparticles for Controlling the Movement of Immune Cells", Nanoscale, May 2015, pp. 7780-7789, vol. 7, No. 17.
Kumar, C.S.S.R., et al., "Magnetic nanomaterials for hyperthermia-based therapy and controlled drug delivery", Advanced Drug Delivery Reviews, 2011, pp. 789-808, vol. 63.
Chen, R., et al., "Wireless magnetothermal deep brain stimulation", Science, Mar. 2015, pp. 1477-1480, vol. 347, Issue 6229.

(56) References Cited

OTHER PUBLICATIONS

Leith, E.N., et al., "Holographic Imagery Through Diffusing Media", Journal of the Optical Society of America, Apr. 1966, pp. 523, vol. 56, No. 4.

Yaqoob, Z., et al., "Optical phase conjugation for turbidity suppression in biological samples", Nature Photonics, Feb. 2008, pp. 110-115, vol. 2.

Yamaguchi, I., et al., "Phase-shifting digital holography", Optics Letters, Aug. 1997, pp. 1268-1270, vol. 22, No. 16.

Schlegel, A., et al., "Optical properties of magnetite (Fe3O4)", Journal of Physics C: Solid State Physics, 1979, pp. 1157-1164, vol. 12.

Ruan, H., et al., "Pulsed ultrasound modulated optical tomography with harmonic lock-in holography detection", J. Opt. Soc. Am. A, Jul. 2013, pp. 1409-1416, vol. 30, No. 7.

Vellekoop, I.M., et al., "Demixing light paths inside disordered metamaterials", Optics Express, Jan. 2008, pp. 67-80, vol. 16, No. 1.

Mooney, R., et al., "Neural Stem Cell-Mediated Intratumoral Delivery of Gold Nanorods Improves Photothermal Therapy", ACS Nano, 2014, pp. 12450-12460, vol. 8, No. 12.

Ruan, H., et al., "Optogenetic Control of Neural Activity with Time-Reversed Ultrasound Encoded Light", Optics in the Life Sciences 2017 (BODA, NTM, OMP, OTA, Brain), pp. 1-3.

Birmingham, K., et al., "Bioelectronic medicines: a research roadmap" Nature Reviews | Drug Discovery, Jun. 2014, pp. 399-400, vol. 13.

Kulkarni, S., et al., "Quantifying the Motion of Magnetic Particles in Excised Tissue: Effect of Particle Properties and Applied Magnetic Field", J. Magn. Magn. Mater., Nov. 2015, pp. 243-252, vol. 393.

Guduru, R., et al., "Magnetoelectric 'spin' on stimulating the brain", Nanomedicine (Lond.), 2015, pp. 2051-2061, vol. 10, No. 13.

Gleich, B., et al., "Tomographic imaging using the nonlinear response of magnetic particles", Nature, Jun. 2005, pp. 1214-1217, vol. 435.

Jang, M., et al., "Method for auto-alignment of digital optical phase conjugation systems based on digital propagation", Optics Express, Jun. 2014, pp. 14054-14071, vol. 22, No. 12.

Wang, D., et al., "Focusing through dynamic tissue with millisecond digital optical phase conjugation" Optica, Aug. 2015, pp. 728-735, vol. 2, No. 8.

* cited by examiner

| Abbreviations | |
|---|---|
| AOM | Acousto-Optic Modulator |
| AP | Aperture |
| BC | Beam Compensator |
| BD | Beam Dump |
| BS | Beam Splitter (50/50) |
| BSP | Beam Splitter (plate type) |
| BST | Beam Splitter (T90/R10) |
| CAM | Camera (CCD) |
| CAMS | Camera (sCMOS) |
| EM | Electro-magnet |
| FC | Fiber Coupler |
| L | Lens |
| LP | Linear Polarizer |
| M | Mirror |
| OBJ | Objective |
| OI | Optical Isolator |
| PBS | Polarizing Beam Splitter |
| PL | Pulsed Laser |
| PLM | Path Length Matching Arm |
| SAM | Sample |
| SH | Shutter |
| SMF | Single Mode Fiber (Polarization Maintaining) |
| SLM | Spatial Light Modulator |
| WP | Half-Wave Plate |

| Light Frequencies | |
|---|---|
| ▬▬ | Laser |
| ▨▨ | Frequency-shifted Light |

| Polarization | |
|---|---|
| ↔ | Horizontal |
| ○ | Vertical |
| ↔ | Unspecified Linear Polarization |

| Run | Mobility | Zeta Potential (mV) | Rel. Residual |
|---|---|---|---|
| 1 | -2.50 | -32.00 | 0.0235 |
| 2 | -2.57 | -32.86 | 0.0209 |
| 3 | -2.64 | -33.73 | 0.0179 |
| 4 | -2.71 | -34.70 | 0.0209 |
| 5 | -2.57 | -32.91 | 0.0158 |
| 6 | -2.71 | -34.68 | 0.0130 |
| 7 | -2.34 | -29.99 | 0.0170 |
| 8 | -2.53 | -32.37 | 0.0309 |
| 9 | -2.45 | -31.31 | 0.0262 |
| 10 | -2.19 | -28.01 | 0.0140 |
| Mean | -2.52 | -32.26 | 0.0200 |
| Std. Error | 0.05 | 0.66 | 0.0018 |
| Combined | -2.52 | -32.24 | 0.0069 |

Fig. 8 a
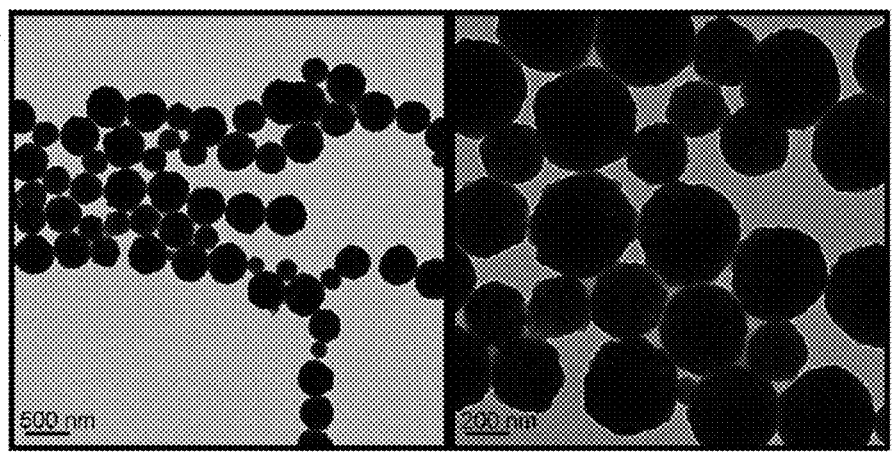
Fig. 8 b
Effective Diameter: 453.6 nm
Polydispersity: 0.031
Baseline Index: 6.0/100.00%
Elapsed Time: 00:05:00
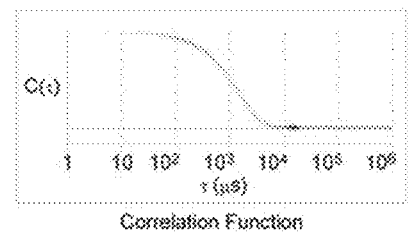
Correlation Function
Fig. 8 c
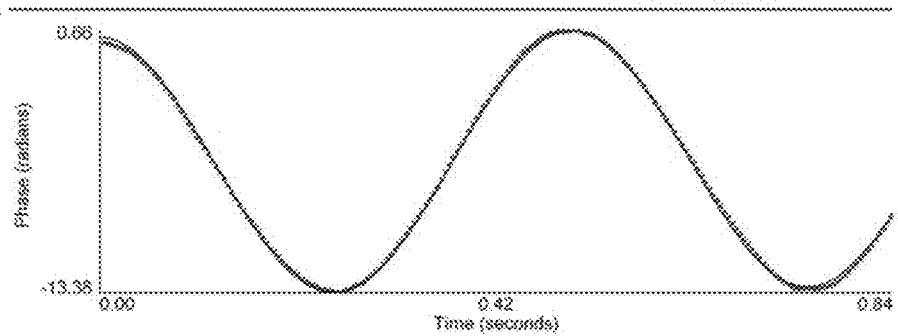
Fig. 8 d
| Run | Mobility | Zeta Potential (mV) | Rel. Residual |
|---|---|---|---|
| 1 | -2.50 | -32.00 | 0.0235 |
| 2 | -2.57 | -32.86 | 0.0209 |
| 3 | -2.64 | -33.73 | 0.0179 |
| 4 | -2.71 | -34.70 | 0.0209 |
| 5 | -2.57 | -32.91 | 0.0158 |
| 6 | -2.71 | -34.68 | 0.0130 |
| 7 | -2.34 | -29.99 | 0.0170 |
| 8 | -2.53 | -32.37 | 0.0309 |
| 9 | -2.45 | -31.31 | 0.0262 |
| 10 | -2.19 | -28.01 | 0.0140 |
| Mean | -2.52 | -32.26 | 0.0200 |
| Std. Error | 0.05 | 0.66 | 0.0018 |
| Combined | -2.52 | -32.24 | 0.0069 |

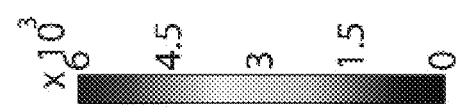
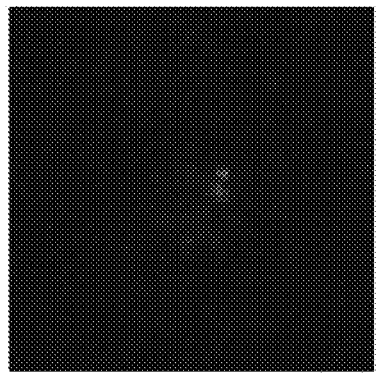
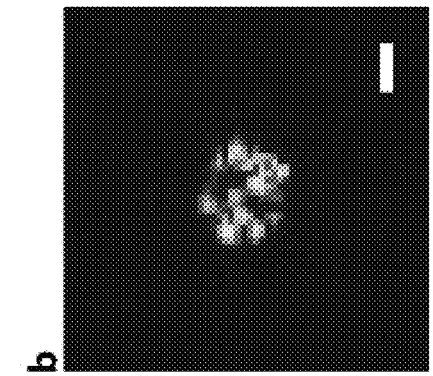
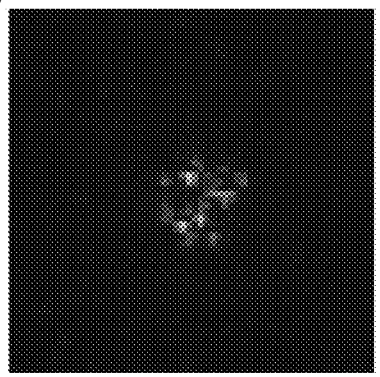
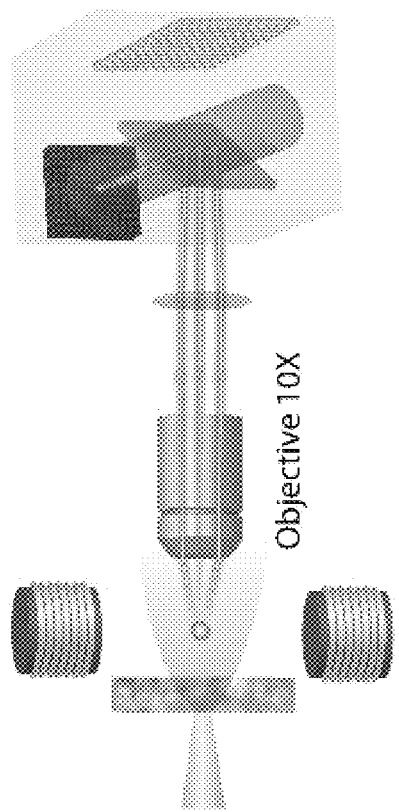
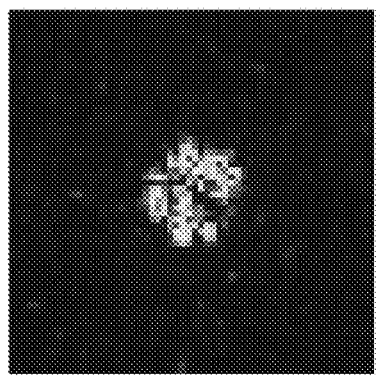
Fig. 10a  Fig. 10b  Fig. 10c  Fig. 10d  Fig. 10e

FOCUSING LIGHT INSIDE SCATTERING MEDIA WITH MAGNETIC PARTICLE GUIDED WAVEFRONT SHAPING

CROSS REFERENCE TO RELATED APPLICATIONS

This application claims the benefit under 35 U.S.C. Section 119(e) of the following and commonly-assigned applications:

U.S. Provisional Patent Application Ser. No. 62/542,656, filed on Aug. 8, 2017, entitled "FOCUSING LIGHT INSIDE SCATTERING MEDIA WITH MAGNETIC PARTICLE GUIDED WAVEFRONT SHAPING," by Haowen Ruan and Changhuei Yang, and U.S. Provisional Patent Application Ser. No. 62/564,850, filed on Sep. 28, 2017, entitled "FOCUSING LIGHT INSIDE SCATTERING MEDIA WITH MAGNETIC PARTICLE GUIDED WAVEFRONT SHAPING," by Haowen Ruan, Changhuei Yang, Jacob Berlin, and Tom Haber;

which applications are incorporated by reference herein.

STATEMENT REGARDING FEDERALLY SPONSORED RESEARCH AND DEVELOPMENT

This invention was made with government support under Grant No. NS090577 awarded by the National Institutes of Health. The government has certain rights in the invention.

BACKGROUND OF THE INVENTION

1. Field of the Invention

This invention relates to a method and system for imaging and focusing electromagnetic radiation in a scattering medium.

2. Description of the Related Art (Note: This application references a number of different publications as indicated throughout the specification by one or more reference numbers within brackets, e.g., [x]. A list of these different publications ordered according to these reference numbers can be found below in the section entitled "References." Each of these publications is incorporated by reference herein.)

The ability to focus light deep inside scattering media such as biological tissue is critical to many applications, such as high-resolution optical imaging, non-invasive optogenetics, light-based therapy, micro-surgery, and optical tweezing. However, the strong optical scattering inherent to many types of biological tissue prevents conventional optics from focusing light beyond depths of ~1 mm, since at this depth nearly all the light has been scattered [1]. To break this optical diffusion limit, wavefront shaping techniques [2-6] are being actively developed to harness the multiply scattered light. These techniques control the optical field on a target plane inside the scattering medium by shaping the optical field on an input plane outside the medium. The relationship between the input plane and target plane can be described by a transmission matrix which characterizes the propagation of light through the scattering medium [7,8].

To gain control over the optical field on the target plane, one needs to measure the transmission matrix. While extensive transmission matrix measurement enables control over a large area on the target plane [9,10], measuring a small part of the transmission matrix is preferable for applications involving highly dynamic samples like living tissue due to the problem of tissue decorrelation [11-13]. A good example is focusing light to a spot inside the scattering sample, in which case one needs to measure only a single row of the transmission matrix [5]. In this instance, one can use either a feedback-based approach to optimize the light intensity at a spot inside the sample [3] or digital optical phase conjugation (DOPC) to directly measure the light field from an embedded point source [14-18]. The latter has an advantage in operation speed as it enables light field measurement in parallel using sensor arrays and therefore shows promise for applications involving dynamic samples.

No matter which method is used to measure the transmission matrix, accessing the target plane is necessary. In practice, however, the target plane inside the scattering medium is often not directly accessible, especially when minimally invasive approaches are desired. To address this problem, conventional approaches resort to indirect access to the target plane by designing a "guidestar" mechanism [5].

Until now, only a few guidestar mechanisms have been reported. These guidestars can be loosely categorized based on their controlling mechanisms. The first category is using light itself to control the guidestar, and includes fluorescence [19,20], second harmonic generation [15], absorption [9, 21-23], and coherence gating [24]. However, fluorescence has low coherence and second harmonic generation is generally inefficient, limiting their working depth with DOPC. Because optical absorption alone cannot generate light for phase conjugation and coherence gating is limited to shallow depths, these approaches are not suitable for DOPC either and have not been used as guidestars for DOPC thus far. The second category employs ultrasound and includes the ultrasound [25-29] and ultrasound microbubble guidestars [30]. While ultrasound offers excellent localization, it also introduces intrinsic drawbacks such as large focal volume, low modulation efficiency, lack of biomolecule specificity, strong attenuation at high frequency, low penetration through some structures like bones or gas, and the need for coupling agents. Although ultrasound microbubbles address the first three problems of the ultrasound guidestar, the microbubbles are largely limited to applications in the vasculature. The third type of guidestar mechanism does not rely on any external driving fields. Instead, it utilizes the intrinsic motion of an object such as a flowing red blood cell [31,32], which largely limits its biomedical applications to the vasculature. Moreover, one cannot freely control the location of the focus.

SUMMARY OF THE INVENTION

To overcome the limitations in the art described above, and to overcome other limitations that will become apparent upon reading and understanding this specification, the present disclosure reports a new category of apparatus implementing a guidestar which uses a magnetic field as the controlling mechanism. The apparatus comprises one or more magnets; and a spatial light modulator or phase conjugate mirror transmitting output electromagnetic radiation having an output field determined from a recording of scattered electromagnetic radiation. The scattered electromagnetic radiation comprises a scattered field formed by scattering from a magnetic particle moving in a scattering medium in response to a magnetic field applied from the one or more magnets. The output electromagnetic radiation having the output field determined from the scattered field forms a focus at the magnetic particle in the scattering medium.

The apparatus can be embodied in many ways including, but not limited to the following.

1. The apparatus further comprising the detector outputting the recording including a signal in response to the scattered electromagnetic radiation received on the detector.

2. The apparatus of one or any combination of the previous embodiments, including a computer connected to the detector and the spatial light modulator.

3. The apparatus of one or any combination of the previous embodiments, wherein the spatial light modulator modulates the output electromagnetic radiation so that the output electromagnetic radiation has the phase and/or amplitude determined by the computer.

4. The apparatus of one or any combination of the previous embodiments, wherein the computer determines the output field comprising a phase conjugate of the scattered field of the scattered electromagnetic radiation.

5. The apparatus of one or any combination of the previous embodiments, wherein the detector comprises a wavefront sensor measuring the phase and/or amplitude of the scattered field and the computer determining the phase conjugate of the phase of the scattered field.

6. The apparatus of one or any combination of the previous embodiments, wherein the one or more signals outputted from detector (in response to receiving the scattered electromagnetic radiation) comprise an interference pattern recording interference between the scattered field and a reference beam incident on the detector.

7. The apparatus of one or any combination of the previous embodiments, wherein the detector comprises a detection system measuring a phase and/or amplitude of the scattered field using phase shifting holography, and the computer determines the output field from the phase and/or amplitude of the scattered field.

8. The apparatus of one or any combination of the previous embodiments, wherein the magnetic field is a time varying magnetic field having a frequency, the scattered field has the frequency or a harmonic of the frequency, and the output electromagnetic radiation has the frequency or the harmonic of the frequency.

9. The apparatus of one or any combination of embodiments 1-7, wherein the scattered electromagnetic radiation comprises first scattered electromagnetic radiation scattered from the magnetic particle at a first position in the scattering medium and comprising a first scattered field, and second scattered electromagnetic radiation (comprising a second scattered field) scattered from the magnetic particle at a second position in the scattering medium after the magnetic particle has moved in response to the magnetic field. The apparatus further comprises the detector detecting the first scattered field and the second scattered field; a circuit or computer connected to the detector determining a difference between the first scattered field and the second scattered field; and the spatial light modulator forming the output field comprising a phase conjugate of the difference.

10. The apparatus of one or any combination of the previous examples, wherein the magnetic particle has a diameter in a range of 2 nm to 50 micrometers, 2 nanometers to 10 nm, 10 nm-50 nm, 50 nm-100 nm, 100 nm-200 nm, 200 nm-500 nm, 500 nm-1 micrometer, 1-10 micrometers, 10-20 micrometers, 30-40 micrometers, or 40-50 micrometers.

11. The apparatus of one or any combination of previous examples, wherein the magnetic particle comprises at least one magnetically responsive metal or material selected from iron, iron oxide, nickel, cadmium, and an alloy of a rare earth metal.

12. The apparatus of one or any combination of previous examples, wherein the magnetic particle comprises a material that interacts with the magnetic field and moves according to a gradient of the magnetic field and/or a magnetically responsive metal.

13. The apparatus of one or any combination of the previous examples, wherein the magnetic particle and the magnetic field are such that the magnetic particle moves a distance between 0 nm and 1 mm (e.g., up to 1 mm) in the scattering medium in response to the magnetic field.

14. The apparatus of one or any combination of the previous examples, wherein the magnetic field has a frequency in a range of 1 Hz-1 MHz.

15. The apparatus of one or any combination of the previous examples, wherein the scattering medium comprises biological tissue including cells mounted on a sample holder coupled to the magnetic field, the detector, and the spatial light modulator of phase conjugate mirror.

16. The apparatus of embodiment 15, wherein the in vivo decorrelation time is reduced to at least 50 milliseconds using an immobilization approach.

17. The apparatus of one or any combination of the previous embodiments, wherein the detector has a frame rate of greater than 20 Hz, the spatial light modulator has response rate of greater than 20 Hz, and the input electromagnetic radiation has an intensity up to 200 mW/cm2 (e.g., for tissue safety).

18. The apparatus of one or any combination of the previous embodiments, wherein the phase conjugate mirror comprises a nonlinear optical device (e.g., photorefractive crystal).

Further disclosed is a method for irradiating a scattering medium, comprising applying a magnetic field to a magnetic particle in a scattering medium so that the magnetic field moves the magnetic particle in the scattering medium; irradiating the magnetic particle in the scattering medium with electromagnetic radiation, wherein the electromagnetic radiation scatters from the magnetic particle so as to form scattered electromagnetic radiation; forming a recording of the scattered electromagnetic radiation on a detector or a phase conjugate mirror; and using the recording to modulate output electromagnetic radiation so that the output electromagnetic radiation comprises an output field determined from the recording and forming a focus at the magnetic particle in the scattering medium.

As a proof-of-concept demonstration, light was focused onto a magnetic particle sandwiched between two pieces of scattering tissue. We then demonstrated that we can also focus light to a targeted cell that has endocytosed magnetic particles. Furthermore, by controlling the position of the particle using an external magnetic field, we demonstrate light focusing to different targeted locations between two pieces of scattering tissue.

BRIEF DESCRIPTION OF THE DRAWINGS

Referring now to the drawings in which like reference numbers represent corresponding parts throughout:

FIG. 1a: A magnetic particle is embedded in a piece of scattering tissue. A portion of the impinging laser beam interacts with the particle and the resulting tagged light is detected interferometrically using the camera of a DOPC system. FIG. 1b: After capturing the field of the tagged light, the conjugate wavefront is displayed on the SLM of the DOPC system. The reconstructed conjugate light field then retraces the scattering paths and forms a focus at the location of the magnetic particle. FIG. 1c and FIG. 1d: Two methods to separate the tagged light field from the background unmodulated light. The field-subtraction method in FIG. 1c captures two optical fields before and after a magnetic field displaces the magnetic particle. The differential field nullifies the contribution from the background that is not scattered by the particle. The frequency-modulation method shown in FIG. 1d uses an AC magnetic field to make the magnetic particle oscillate, which shifts the frequency of the light that interacts with the particle. By matching the frequency of a planar reference beam with that of the tagged light, the DOPC system detects the tagged light field via phase-shifting holography. FIG. 1e After imprinting the conjugate wavefront of the tagged light on a planar reference beam using the SLM, the conjugate wave forms a bright focus on top of a dim background at the location of the magnetic particle inside the scattering medium.

FIG. 2a: Schematic of the setup to record the field of the tagged light. FIG. 2b: Schematic of the setup for playback of the tagged field and observation of the focus. In this step, the tissue on the left side was removed and an imaging system was used to observe the light intensity distribution on the magnetic particle plane. FIGS. 2c and 2d: Bright-field images of the particles with the magnetic field in different directions. FIG. 2e: The focus observed with the setup shown in FIG. 2b.

FIG. 3b: 50 Hz (2nd harmonic), and FIG. 3c: 75 Hz (third harmonic) relative to the laser frequency. FIG. 3d: Control experiment: No focus was observed when the reference beam frequency was shifted by 30 Hz (frequency mismatch). Scale bar: 5 µm.

FIGS. 4a, 4b: Bright-field images of a cell under two magnetic fields. FIG. 4c: Focus achieved by the field-subtraction method. FIG. 4d: Focus achieved by the frequency-modulation method (fm=25 Hz).

FIGS. 7a-7c. Characteristics of polystyrene core paramagnetic particles. FIG. 7a: Transmission Electron Microscope (TEM) images of the polystyrene core paramagnetic particles (Scale bar=2 µm and 1 µm respectively) FIG. 7b: Zeta potential of the polystyrene core paramagnetic particles (mV); FIG. 7c: table containing Zeta potential and mobility.

FIGS. 8a-8c. Characteristics of carboxyl superparamagnetic nanoparticles. FIG. 8a: TEM images of the carboxyl superparamagnetic nanoparticles (Scale bar=500 nm and 200 nm respectively). FIG. 8b: Hydrodynamic size (nm) of the carboxyl superparamagnetic nanoparticles and FIG. 8c: Zeta potential of the carboxyl superparamagnetic nanoparticles (mV).

FIG. 8d. Table containing Zeta potential and mobility for superparamagnetic nanoparticles.

FIGS. 10a-10d| Measurement of the light-tagging efficiency of the magnetic particle guidestar based on the magnetic particle labelled cell sample. FIG. 10a: Schematic of the setup to measure the light-tagging efficiency of the field-subtraction method and the frequency-modulation method. The light-tagging efficiency was calculated by the ratio between the power of the tagged light and the power of the light passing through the cell with magnetic particles. FIG. 10b: The tagged light field measured by the field-subtraction method, from which we calculated the light-tagging efficiency to be 29%. FIGS. 10c-10e: The tagged light fields measured by the frequency-modulation method, when the reference beam frequency was shifted by FIG. 10c: 25 Hz (the fundamental frequency shift of the modulated light), FIG. 10d: 50 Hz (2nd harmonic), and FIG. 10e: 75 Hz (3rd harmonic) relative to the laser frequency. The light-tagging efficiency calculated from the measured field in (c) is 5%. Scale bar: 5 µm.

DETAILED DESCRIPTION OF THE INVENTION

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Technical Description

A. Example Apparatus

Figure 1:
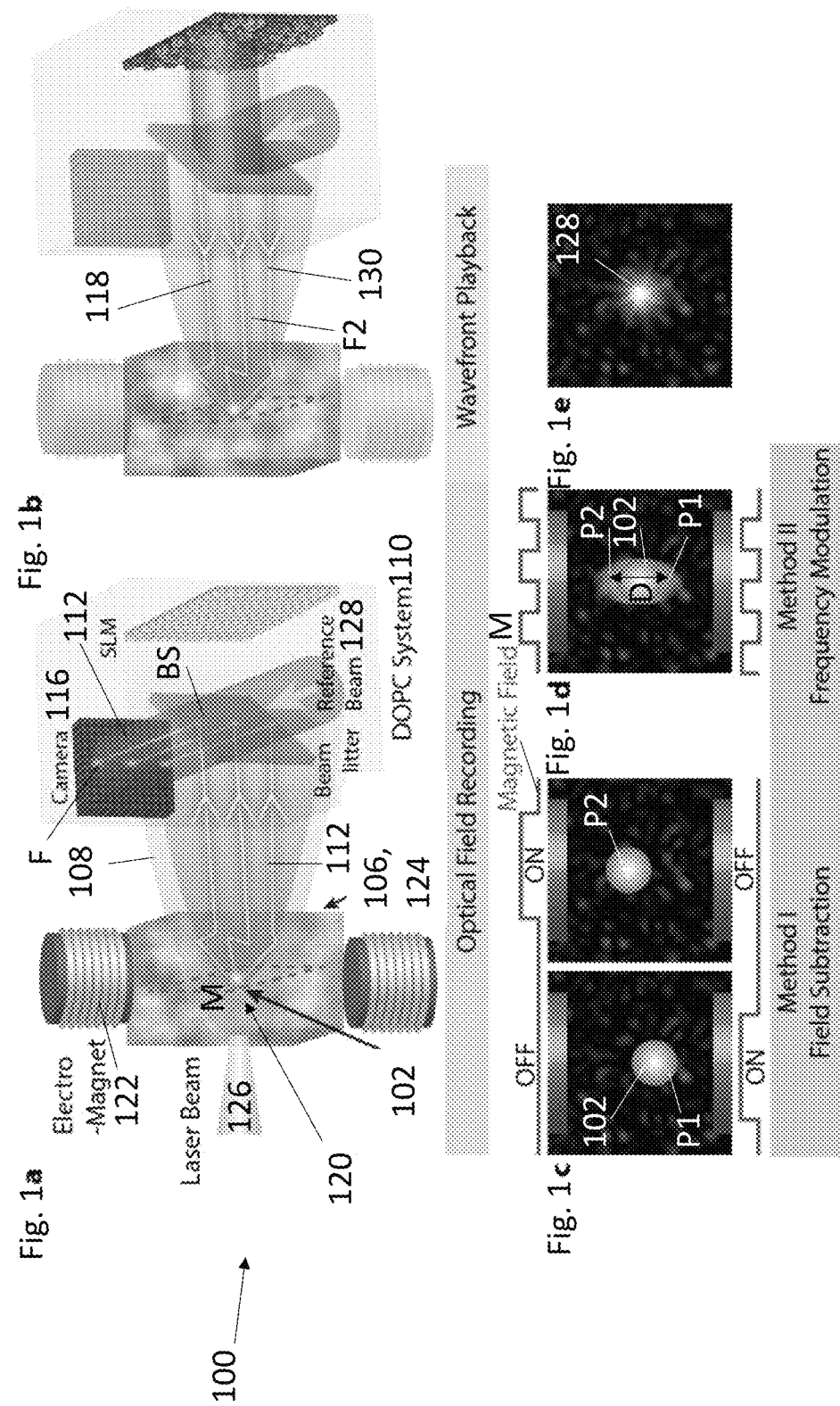
FIGS. 1a-1e. Principle of magnetic particle guided optical focusing.
Figure 6A:
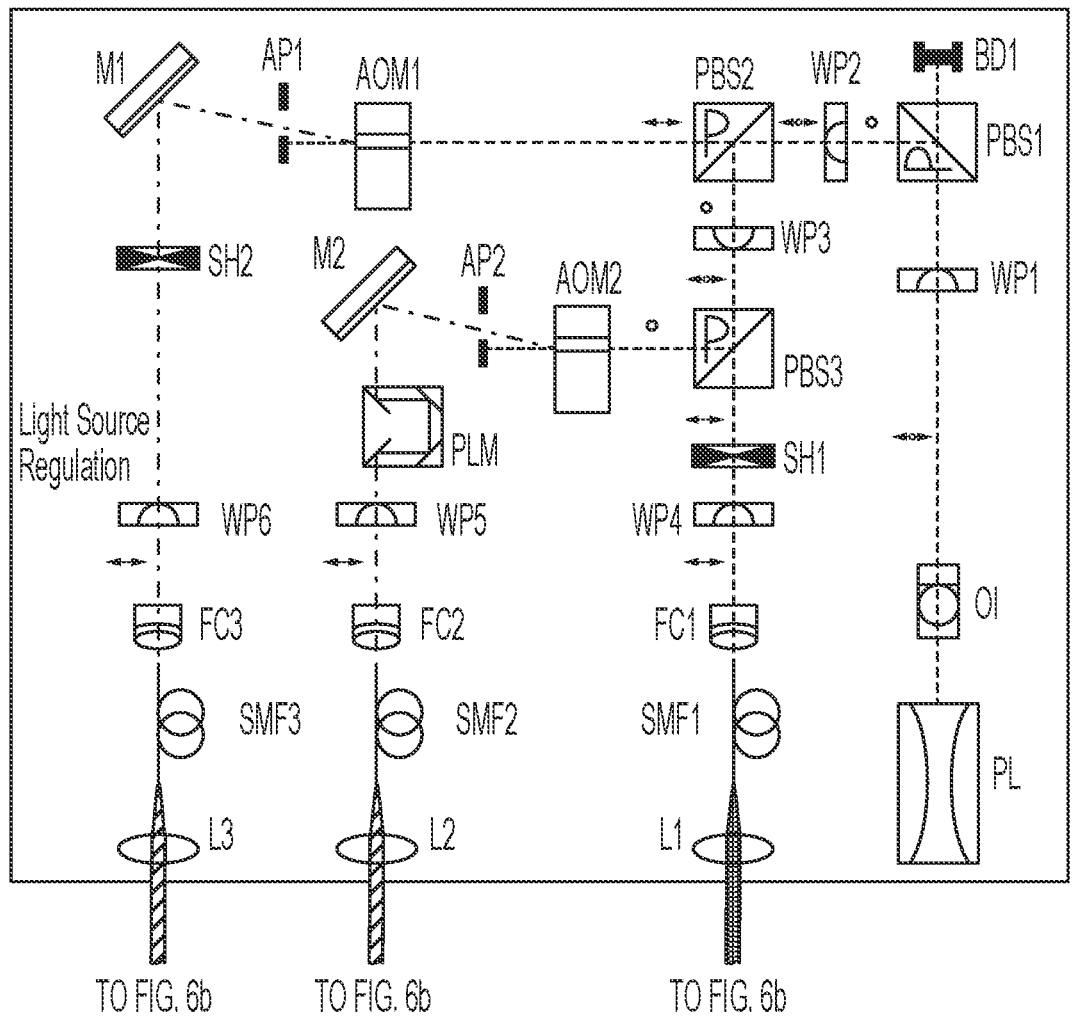
FIG. 6 is a schematic of the setup used to obtain data presented herein.
Figure 6B:
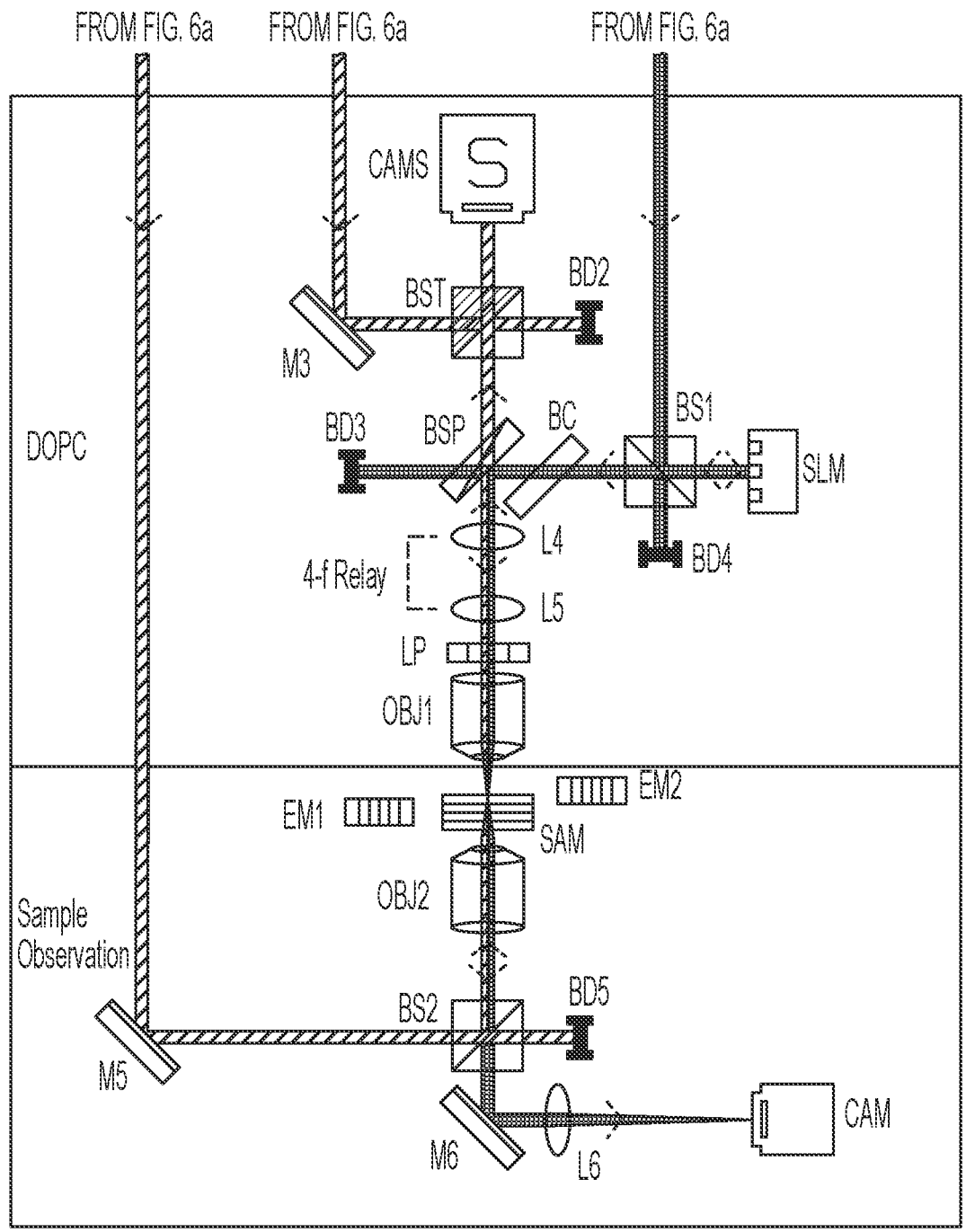

The basic operation of an apparatus 100 using a magnetic particle 102 guidestar is illustrated in FIG. 1a (see Supplementary FIG. 6 for a more detailed setup example). As light 104 travels into the biological tissue 106, its beam size is broadened in space due to multiple scattering (FIG. 1a). As it passes through the tissue 106, part of the scattered light 108 interacts with the magnetic particles 102 embedded deep inside the tissue 106. A detection system 110 selectively detects light 112 that interacts with the magnetic particles 102 such that the magnetic particle 102 is effectively a light source or guidestar 114 embedded inside the tissue 106 [5]. In the example of FIG. 1a, the detection system 110 comprises a DOPC system including a detector 116 (e.g., camera) electromagnetically coupled to a spatial light modulator SLM. Once the DOPC system measures the light field F from the guidestar 114, it reconstructs a phase conjugated copy 118 that retraces the scattering trajectories back to the location 120 of the guidestar, based on the principle of optical phase conjugation [37,38] (FIG. 1b). The phase conjugated copy 118 forms a focus 128 of output electromagnetic radiation 130 at the location of the magnetic particle 102. The present disclosure reports on two methods allowing the DOPC system to selectively detect the light 112 that interacts with the magnetic particles 102. The apparatus further includes one or more magnets 122 (e.g. electromagnets) positioned to apply a magnetic field M to the magnetic particle 102 in the scattering medium 124 so that the magnetic field M moves the magnetic particle 102 in the scattering medium 124. A source of input electromagnetic radiation irradiates the tissue 106 and magnetic particle 102 with electromagnetic radiation 126 (e.g. laser beam). A beamsplitter BS directs the light 112 and a reference beam 140 onto the camera 116 so as to measure the field/wavefront of the scattered light 112.

B. Example: Field-Subtraction Method

The first method is called "field subtraction". In this method, a magnetic field M is used to displace D the magnetic particle 102, which alters the optical field of laser beam 126 that interacts with the magnetic particle 102 (FIG. 1c). By taking the difference between the two optical fields F measured before (first position P1) and after (second position P2) displacing the magnetic particle, we were able to measure the optical field modulated by the particle displacement. Mathematically, the first optical field on the target plane Et_1(x, y) can be decomposed into a background field Eb(x, y) that does not interact with the particle, and a modulated field that interacts with the particle Em_1 (x, y), yielding Et_1(x, y)=Eb(x, y)+Em_1(x, y).

In one or more embodiments using DOPC, it is more convenient to discretize the functions into column vectors (i.e. Et 1=Eb+Em_1), each of which contains n complex elements. In this representation, each element in the column vector maps to an optical mode on the two-dimensional target plane. Similarly, we can describe the second field as Et_2=Eb+Em_2, where Et_2 is the field at the target plane and Em_2 is the field that interacts with the particle after it was displaced by the external magnetic field. The light fields measured on the camera plane (or input plane) can be connected to the optical fields on the target plane through a transmission matrix T such that E1=TEt_1=T(Eb+Em_1) and E2=TEt_2=T(Eb+Em_2). Here, T is an m×n matrix whose elements follow a circular Gaussian distribution and E1 and E2 are column vectors of m elements, where each element represents an optical mode on the camera plane before and after particle displacement, respectively. Taking the difference between these two measured fields, we have ΔE=E2−E1=T(Em_2−Em_1). Here, the field subtraction effectively removes the background field on the measurement plane, resulting in a field that describes the modulation by the magnetic guidestar. Finally, the conjugated differential field ΔE* is played back with an optical gain a provided by the playback beam (where * denotes conjugate transpose). Assuming time-reversal symmetry, we can calculate the resulting playback field Ep on the target plane by multiplying T from the left with ΔE*:

$$E_p = \alpha \Delta E^* T \quad (1)$$
$$= \alpha[(E_{m\_2}^* - E_{m\_1}^*)T^*]T$$
$$= \alpha\beta(E_{m\_2}^* - E_{m\_1}^*).$$

Here, we assume minimal absorption within the sample to apply the approximation T*T≈βI, where β is the fraction of scattered light that is measured by the DOPC system and I is an identity matrix. The playback light effectively cancels out the random transmission matrix to refocus at the locations of the magnetic particle.

In embodiments described herein, we moved the magnetic particles by changing the direction of the magnetic field and the field gradient using a pair of electromagnets (FIG. 1c and FIG. 6), and captured the light fields exiting the scattering media before and after particle displacement using four-step phase-shifting holography [39]. Then, by subtracting these two measured fields, the background light field not diffracted by the particles is cancelled, and we can obtain the field of the tagged light.

C. Example: Frequency-Modulation Method

A second method to measure the wavefront of the light tagged by the magnetic particle is called "frequency modulation". In this method, we generated an alternating current (AC) magnetic field that produced a time-varying magnetic field gradient to oscillate the magnetic particles (FIG. 1d). In one or more examples, the magnetic particles contain iron oxide that has strong absorption at the 532 nm wavelength of the laser (Absorption coefficient ~$10^5$ cm$^{-1}$ [40]), so that the motions of the particles mainly modulate the amplitude of the light that interacts with them. Based on this assumption, the optical field of the modulated light, as a function of time, can be expressed as $$E_m(t) = f(t)A\exp[-i(2\pi f_0 t + \varphi_0)], \quad (2)$$

where $f_0$ is the laser frequency, A and $\varphi_0$ are the amplitude and phase of the light, respectively, and f (t) is a rectangular modulation function with a fundamental frequency of fm, a pulse duration of τ, and an initial phase φm. To analyze the spectral composition of f (t), the f(t) can be expanded into a Fourier series:

$$f(t) = \sum_{n=1}^{\infty} \frac{\sin(\pi n \tau f_m)}{n\pi} \times \{\exp[-i(2\pi n f_m t + \varphi_m)] + \exp[i(2\pi n f_m t + \varphi_m)]\} + \tau f_m. \quad (3)$$

By substituting f(t) into Em(t) in Eq. 2, we obtain:

$$E_m(t) = \sum_{n=1}^{\infty} \frac{A}{n\pi}\sin(\pi n \tau f_m)\exp\{-i[2\pi(f_0 + nf_m)t + \varphi_0 + \varphi_m]\} + \sum_{n=1}^{\infty} \frac{A}{n\pi}\sin(\pi n \tau f_m)\exp\{-i[2\pi(f_0 - nf_m) + t + \varphi_0 - \varphi_m]\} + \tau f_m A\exp[-i(2\pi f_0 t + \varphi_0)]. \quad (4)$$

From Eq. (4), we can see that the frequency of the portion of the light field that interacted with the particle is shifted by ±nfm. It should be noted that in practice the modulation mechanisms also include phase modulation, since the particle motion also alters the optical path-length. In this case, the phase modulation also generates harmonic side bands. Therefore, to measure the wavefront of the tagged light out of the background (whose frequency is f0), we can simply tune the frequency of the reference beam to one of the frequencies of the tagged light and perform four-step phase-shifting holography [39,41]. Then, using the SLM inside the DOPC system, we can generate the phase conjugate light field, which will focus to the location of the magnetic guidestar deep inside the scattering medium (FIG. 1e).

C. Example Results

Figure 7A:
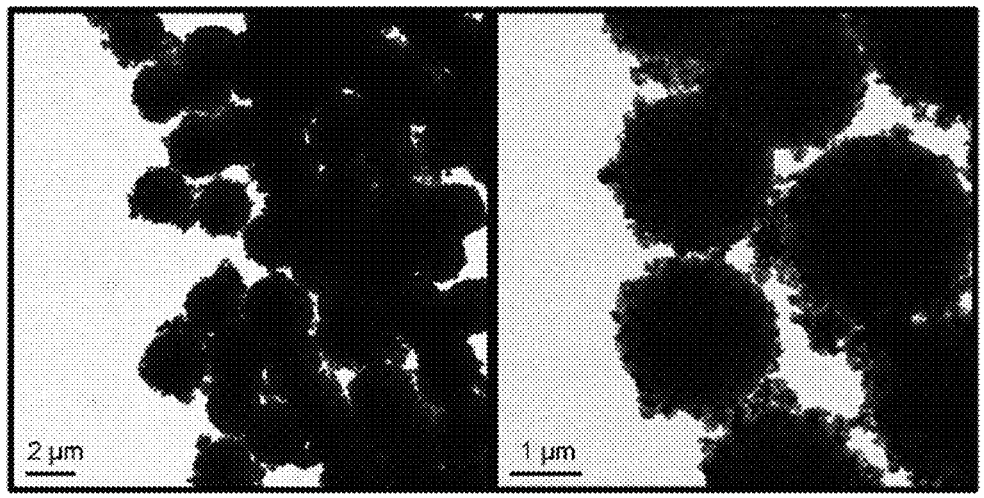
Figure 7B:
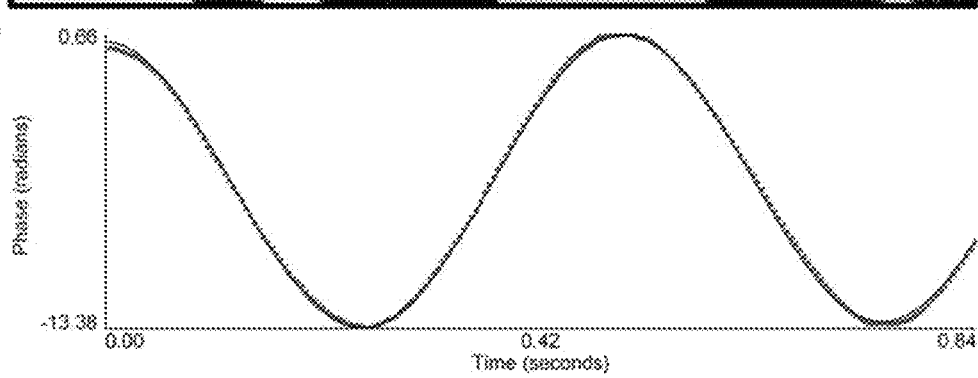

1. Focusing Light Inside Scattering Media Using Magnetic Particle Guided Optical Phase Conjugation To demonstrate magnetic particle guided optical focusing, we modified the system shown in FIG. 1a-1b, to enable direct observation of the light intensity at the target plane (FIG. 2a-2b). In this case, the magnetic particles (2.5 µm mean diameter, see FIG. 7a-7c for particle characterization) were placed in a microfluidic channel that was embedded between two pieces of 1 mm thick chicken breast tissue (see section D2 for sample preparation). The tissue on the observation system side (the left side as shown in FIG. 2a-2b) can be translated in and out of the system to allow the magnetic particles and the light intensity to be directly observed using an imaging system (FIG. 2b, see also FIG. 6 for a detailed setup).

Figure 2:
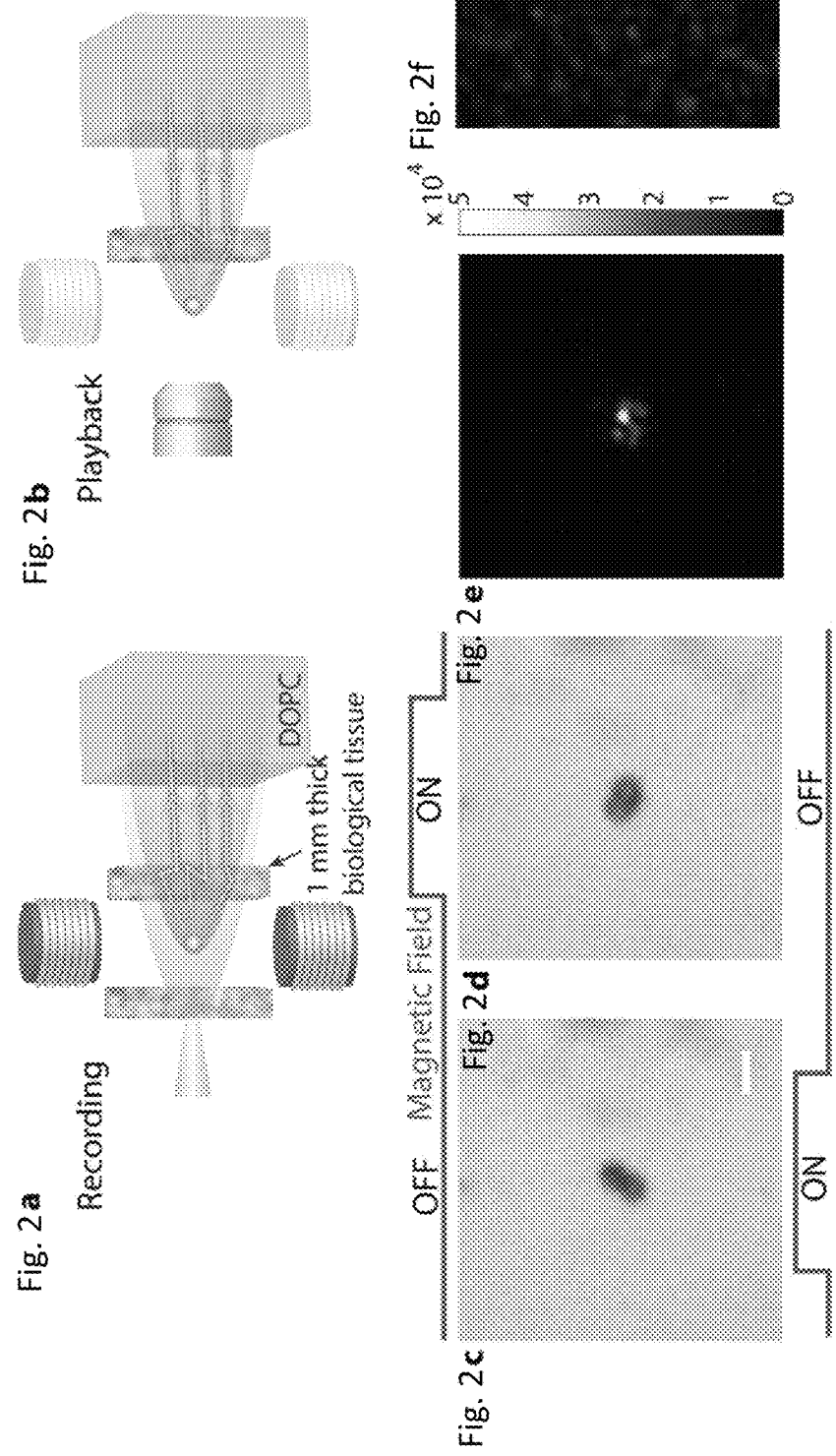
FIGS. 2a-2e. Magnetic particle guided optical focusing with the field-subtraction method.
(FIG. 2f: Control experiment: No focus was observed when we turned off the magnetic fields and repeated the experiment. Scale bar: 5 µm.

We first demonstrated optical focusing through the scattering medium using the field-subtraction method. To observe the particle displacement due to the switching of the external magnetic field, we directly imaged the magnetic particles as shown in FIGS. 2c and 2d. The measured displacement of the particles was 1.7 µm. We then put the tissue back in place (FIG. 2a) and implemented the field-subtraction method to measure and compute the playback light field. A strong focus can be directly observed through the imaging system (FIG. 2, b and e). As a control, we turned off both magnetic fields and repeated the experiment, and no observable focus was created (FIG. 2f).

We quantified the focus created by using the field-subtraction method. Here, we selected a column across the pixel of maximum intensity out of the image (FIG. 2e) and fitted this column with a Gaussian profile. We then took the amplitude of the Gaussian profile as the peak intensity. To calculate the background intensity, we shifted the pattern on the SLM by 10 pixels in both directions to break the phase conjugation relationship, resulting in a background image. The background intensity was then calculated by taking the mean intensity of this image. The peak intensity to background ratio (PBR) of the focus shown in FIG. 2e is 140±4, which is one to two orders of magnitude higher than those achieved with the ultrasound guidestar [26,27]. The full width at half maximum (FWHM) of the focus, which is defined as the FWHM of the fitted Gaussian profile, is 1.24±0.04 µm, which is ~25 times smaller than the size of the ultrasound guidestar. The error estimation is based on the 95% confidence bounds of the fitting. The magnetic guidestar has a similar performance in terms of both PBR and resolution compared to the ultrasound microbubble guidestar, because both methods involve the use of micron-scale physical guidestars.

Figure 3:
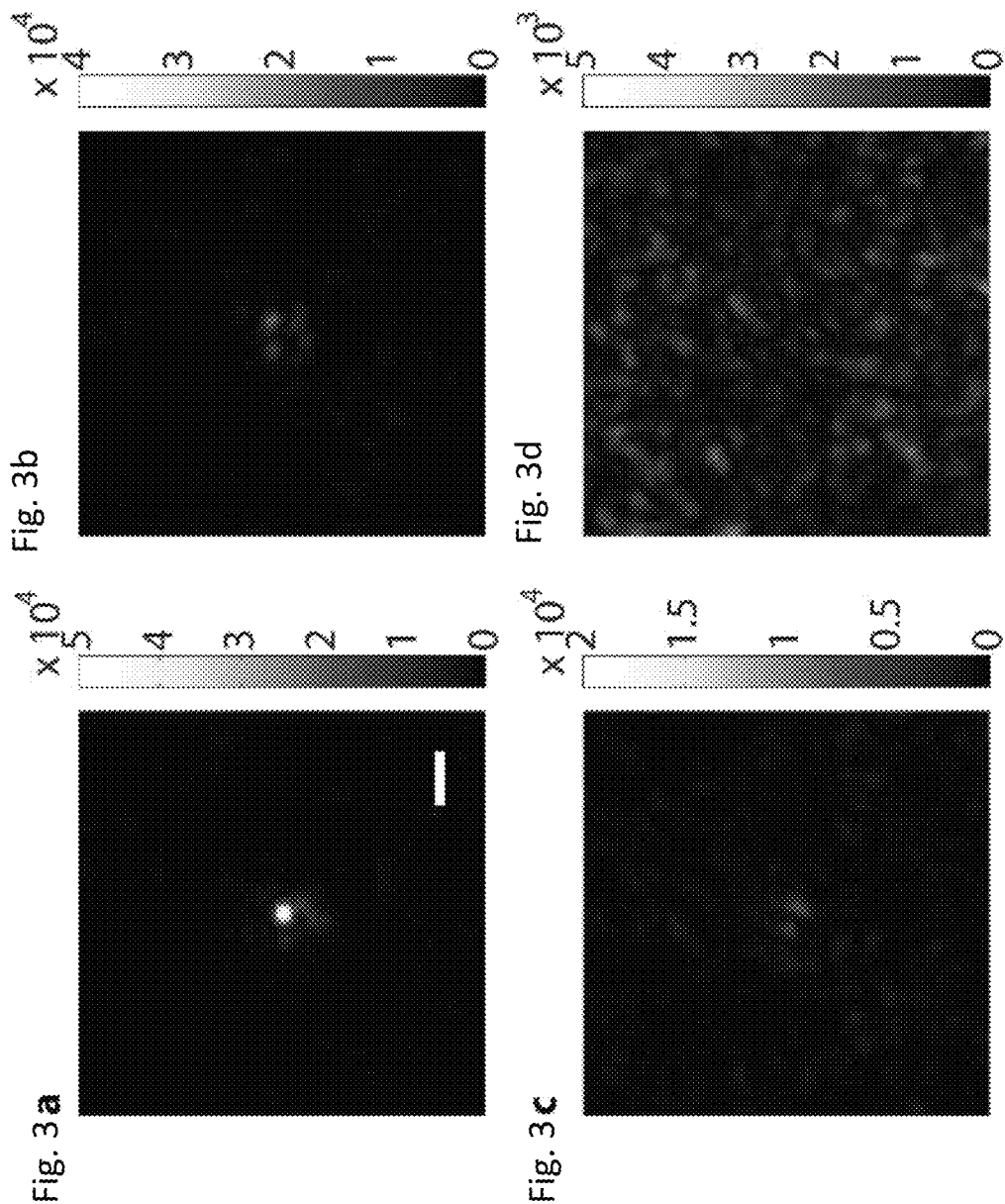
FIGS. 3a-3d. Magnetic particle guided optical focusing with the frequency-modulation method. The electromagnets were driven by 25 Hz rectangular waves. Images were captured with the setup shown in FIG. 2b. The focus achieved when the reference beam frequency was shifted by FIG. 3a: 25 Hz (fundamental frequency)

We also demonstrated optical focusing with the frequency-modulation method using the same setup. Here, we drove two electromagnets with 25 Hz rectangular waves (fm=25 Hz, duty cycle=40%, power=6 W) with a π phase shift between the two signals. To measure the magnetic guidestar tagged light, we also shifted the frequency of the reference beam by 25 Hz using an acousto-optic modulator. The playback light focus is shown in FIG. 3a. To verify the generation of higher harmonic modulated signals, we also shifted the frequency of the reference beam by 50 Hz (second harmonic) and 75 Hz (third harmonic) and measured the corresponding light fields. The playback light also forms foci through the scattering medium but becomes weaker with higher harmonics (FIGS. 3b and 3c). As a control, we shifted the reference beam frequency by 30 Hz (≠nfm) and no observable focus was made (FIG. 3d) due to the frequency mismatch between the tagged light and the reference beam. Using the same method to quantify the focus created with the fundamental frequency, we found that the PBR of the focus in FIG. 3a is 128±6 with a focal spot size of 1.44±0.08 µm.

2. Focusing Light onto Magnetic-Particle-Tagged Cells Inside Scattering Media

The magnetic particle guidestar can be used for optical targeting of cells of interest, for applications such as photothermal or photodynamic therapy. In this scenario, specific cells can be targeted by the magnetic particles through endocytosis or membrane attachment. Then, by performing magnetic particle guided focusing, we can find the correct wavefront solution to allow light to be focused to the desired cell, even when the cell is located deep inside scattering tissue.

Figure 4:
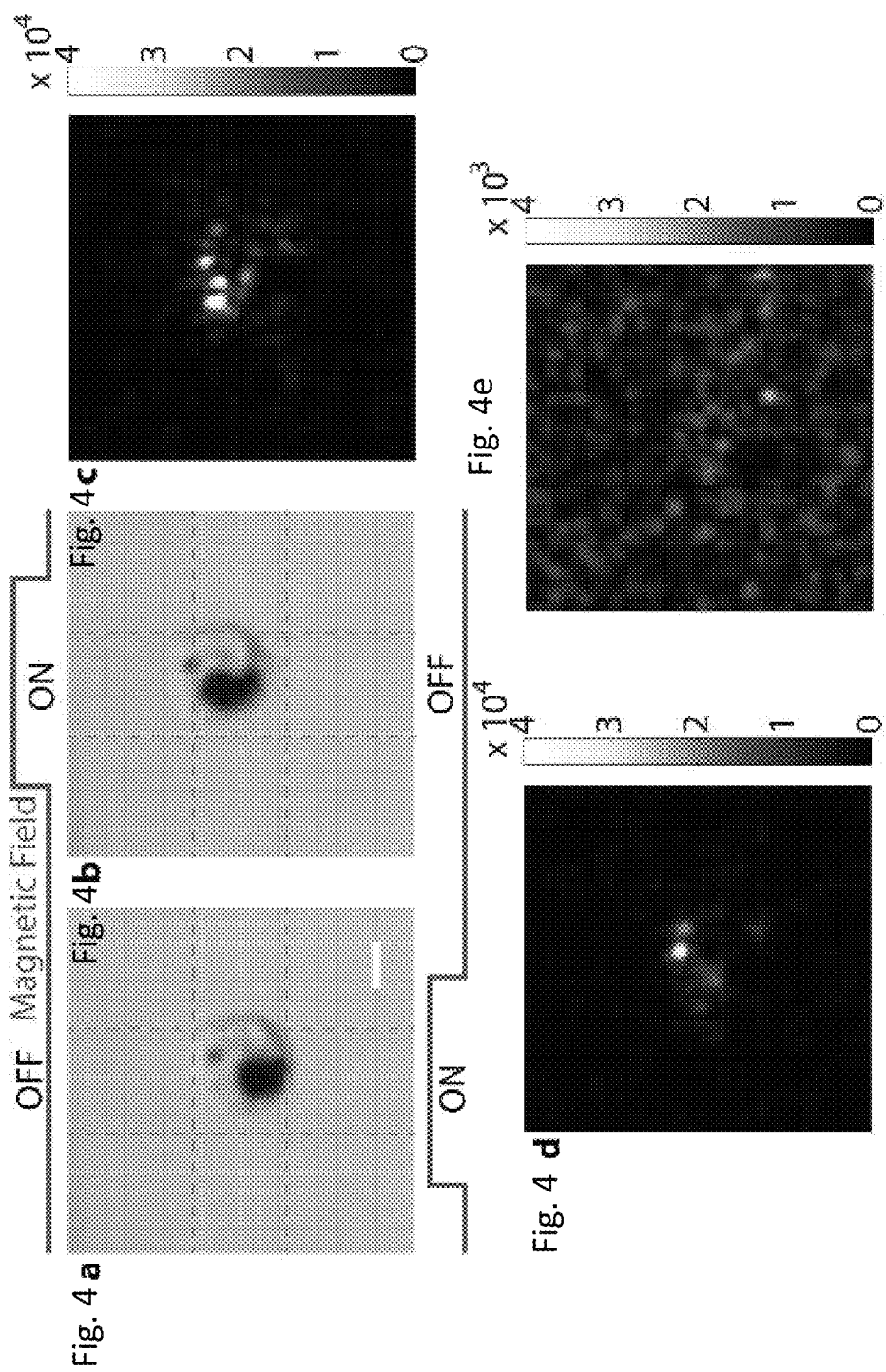
FIGS. 4a-4d. Focusing light onto a targeted cell that endocytosed 453-nm diameter magnetic particles.
FIG. 4e: Control experiment: No focus was observed when we circularly shifted the SLM pattern by 10×10 pixels after obtaining the result in FIG. 4d. Scale bar: 5 µm.

Described herein is a proof-of-concept experiment based on macrophage cells because macrophages readily endocytose nanoparticles and are the primary cells in the body for the initial uptake of nanoparticles. We added the magnetic particles (453 nm mean diameter, see FIGS. 8a-8d for particle characterization) to the cells (see Section D2 for sample preparation and FIG. 9 for cell viability measurement results). After the cells engulfed the particles, the sample was loaded into a microfluidic channel. FIGS. 4a-4b show bright-field images of a cell that endocytosed the magnetic particles as it was being driven by magnetic fields of two different directions, respectively. The observable displacement of 2.2 µm shows great promise for focusing light using the field-subtraction method. Based on this mechanism, we were able to focus light between two pieces of 1-mm thick tissue (FIG. 4c). We also demonstrated optical focusing using the frequency-modulation method, in which we used a 25 Hz AC magnetic field to oscillate the magnetic particles. By measuring the frequency-shifted light, we were able to focus light to the cell with magnetic particles (FIG. 4d). As a control, when we shifted the phase pattern displayed on the SLM by 10 pixels in both directions, we observed a background image without a discernable focus (FIG. 4e). The PBRs of the foci achieved by the two methods were 125±2 and 95±2, respectively, based on the aforementioned calculation method.

3. Focusing Light to Different Target Locations Inside Scattering Media

Figure 5:
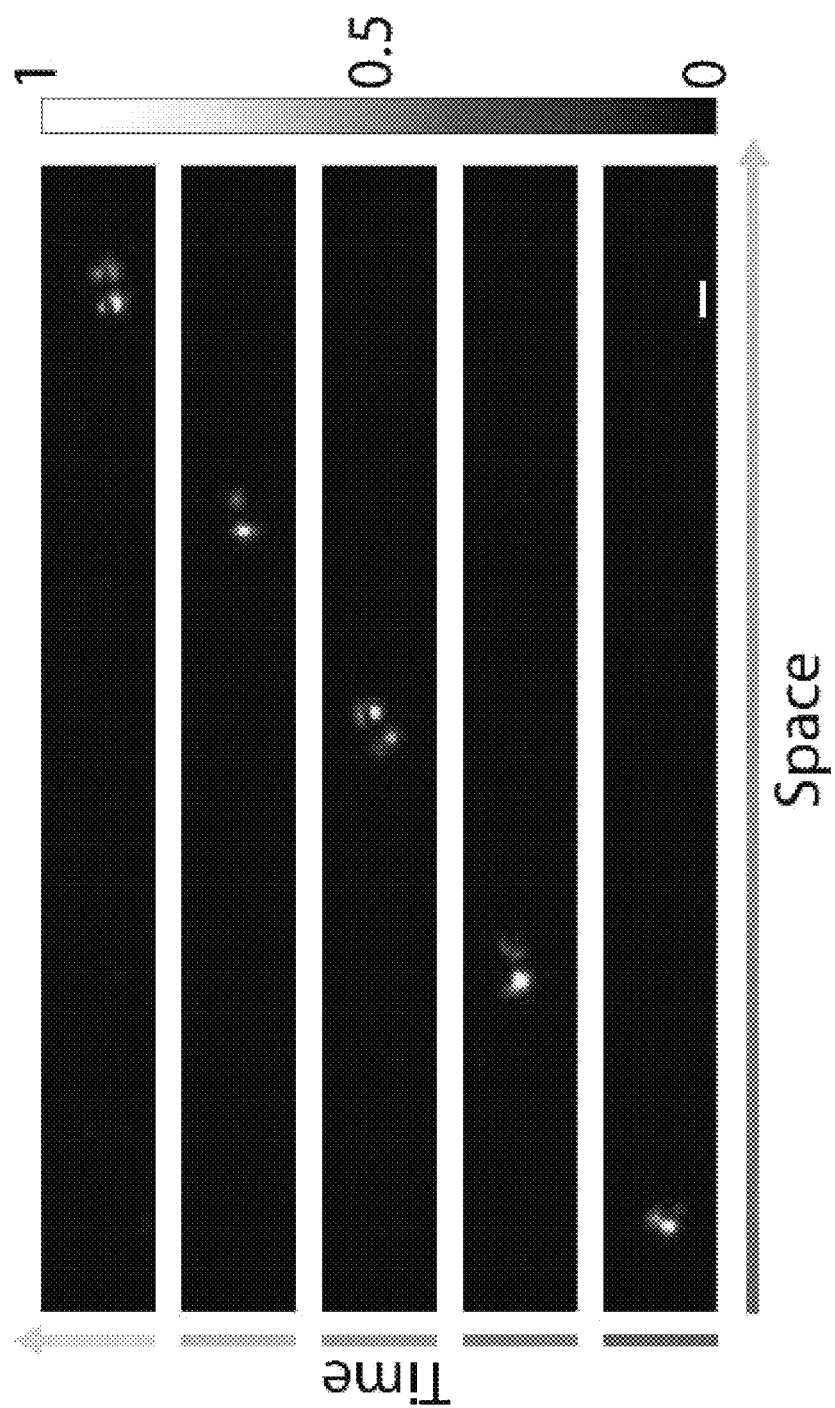
FIG. 5. Focusing light to different target locations by controlling the positions of the magnetic particles using an external magnetic field. The magnetic particles were driven to the target locations inside a microfluidic channel based on the position feedback from the observation microscope (FIG. 2b). After reaching each target location, the magnetic particles were covered by the scattering samples on both sides as shown in FIG. 2a, and the DOPC process was implemented to create a focus through the scattering sample on the DOPC system side. Then, the scattering sample on the observation microscope side was removed (FIG. 2b) and the focus can be observed directly. Scale bar: 5 µm.

In contrast to conventional physical guidestars which limit the optical focus to a fixed location, the magnetic guidestar is able to relocate to a target position by controlling the external magnetic field. As a proof-of-concept demonstration, we used a magnet to move the magnetic particles in 50% glycerol through a microfluidic channel to a target location monitored through a wide-field microscope as shown in FIG. 2b. We then sandwiched the sample between two pieces of 1 mm thick chicken tissue (FIG. 2a) and implemented the frequency-modulation method to focus light to the particles. The above process was repeated five times to form foci at five target locations along a line with a step size of 30 µm. The image of the focus at each location is shown in FIG. 5.

D. Further Experimental Details for the Data Presented Herein

1. Apparatus

The experimental setup can be divided into three modules as shown in FIG. 6. The first module, named Light Source Regulation, prepares three light beams for the experiment, a sample beam, a reference beam, and a playback beam. These three beams share the same light source, the pulsed laser (532 nm wavelength, 20 ns pulse width, 40 kHz rep rate, QL532-500-RL, CrystaLaser). It should be noted that the principle of this work does not depend on the pulsed nature of the illumination and would also work with a continuous wave (CW) laser source. Both the reference beam and the sample beam are shifted in frequency using two acousto-optic modulators (AOM, AFM-502-A1, IntraAction), respectively. All these three beams are spatially filtered, collimated, and aligned to the same polarization direction as that of the spatial light modulator (SLM, Pluto, Holoeye).

The second module is the DOPC system. This system consists of two key components, a camera (PCO.Edge, PCO) and an SLM, which are precisely aligned to each other through a plate beam splitter (BSP). A path length compensator is used to match the path length of different k-vectors of the sample beam and playback beam. A pair of lenses (focal length of L4: 200 mm, L5: 75 mm) in a 4-f configuration images the back focal plane of the objective (10×, 0.25 NA, Plan N, Olympus) to the camera. The measured speckle size is on average 9 SLM pixels, resulting in $\sim 2.2 \times 10^5$ controlled optical modes with the SLM which contains 2 million pixels. A four-phase stepping approach is used to measure the optical field from the sample. The DOPC system alignment is based on the method described previously in reference [1]. The third module is called Sample Observation as shown in FIG. 6. In this module, the sample beam is routed to the sample placed between two electromagnets (cylindrical solenoid, 32 mm diameter, 31 mm height, 24 V, 6 W, UE 3231, UE-TECH). The measured peak magnetic field and field gradient amplitude at a position 10 mm away from the magnet surface (sample position) is 17.3 mT and 27.4 mT/mm, respectively. The magnetic field was measured using a Gaussmeter (AlphaLab Inc., GM3). To optimize the magnetic particle displacement, one magnet is placed slightly off axis with reference to the other as shown in FIG. 6 to provide a torque for particle rotation. The magnetic particles and the playback light are observed using a microscopic imaging system consisting of an objective (20×, 0.25 NA, SLMPlan N, Olympus), a tube lens (L6, focal length: 200 mm), and a camera (Stingray F145, Allied Vision Technologies).

The measured size of the optical speckle on the target plane was on average 1.5 μm. The number of optical modes being modulated can be estimated based on the mean size of the speckle grain, the size of the target, and its displacement using the following equation, $$M \approx \frac{2ndl_{tg}}{l_{sp}^2},$$

where n is the number of targets along the direction orthogonal to the direction of target displacement; d is the amplitude of target displacement; $l_{tg}$ is the length of the target; $l_{sp}$ is the mean diameter of the speckle. For the 2.5 μm magnetic particles shown in FIGS. 2a-2f, we have n=2; d=1.7 μm; $l_{tg}$=2.5 μm, resulting in M≈8. For the cell with magnetic particles, we have n=1; d=2.2 μm; $l_{tg}$=11 μm, resulting in M≈22.

2. Sample Preparation

For the experiments without living cells, we used polystyrene core paramagnetic particles with a mean diameter of 2.5 μm (PM-20-10, Spherotech). We added 1 μl of the magnetic particle solution (2.5% w/v) into 0.5 ml water, resulting in a concentration of 0.05 mg/ml. This sample was perfused into a rectangular microfluidic channel with a cross section of 50 μm×500 μm (VitroTubes, VitroCom).

For the experiments involving living cells, we used carboxyl superparamagnetic particles of 453 nm mean diameter (CM-05-10H, Spherotech). We mixed 2 μl of the magnetic particle solution (1% w/v) with 1 ml culture medium (Dulbecco's Modified Eagle's Medium (DMEM) with 10% Fetal Bovine Serum (FBS) and 1% Penicillin and Streptomycin (PS)) and then added the mixed solution to the macrophages (RAW 264.7) in a cell culturing dish (35 mm diameter) containing 4 ml culture medium. The initial confluency of the cell sample was ~15%. After culturing for ~36 hours, some of the macrophages engulfed the magnetic particles, and the cell confluency reached ~90%. We then harvested the cells. The media was removed and replaced with 0.5 ml trypsin-EDTA (0.05%, Gibco) and incubated in the incubator for an additional 5 mins. After the cells detached from the plate surface, the sample was transferred into a micro centrifuge tube using a pipette. The sample in the micro centrifuge tube was centrifuged for 3 mins at 4000 rpm. The trypsin-EDTA on top of the cell pellet was replaced with 0.5 ml fresh culture medium. Then the sample was mixed and perfused into a microfluidic channel of the same model as described in the last paragraph. In our experiment, ~10% of the cells engulfed sufficient magnetic particles to generate significant guidestar effect under the external magnetic fields.

The scattering sample was made of 1-mm-thick chicken breast tissue (1 mm×6.3 mm×6.3 mm). The sliced tissue was sandwiched between a 1-mm-thick glass slide and a 0.17 mm thick coverslip with a 1-mm-thick spacer in between. The samples were then sealed to avoid dehydration during the experiment.

3. Magnetic Particle Characterization

Dynamic light scattering (DLS) and Zeta potential measurements were performed on a Brookhaven 90 Plus/BI-MAS Instrument (Brookhaven Instruments, New York). DLS measurements were obtained by performing 5 runs at 30 s per run and Zeta potential measurements were obtained by performing 10 runs with 30 cycles per run.

Transmission electron microscopy (TEM) images were obtained with an FEI Tecnai T12 transmission electron microscope at an accelerating voltage of 120 keV and images were taken with a Gatan Ultrascan 2K CCD camera. The nanoparticle samples were imaged on 300 mesh carbon/formvar coated grids (Ted-Pella).

4. Cell Viability Measurement

Figure 9:
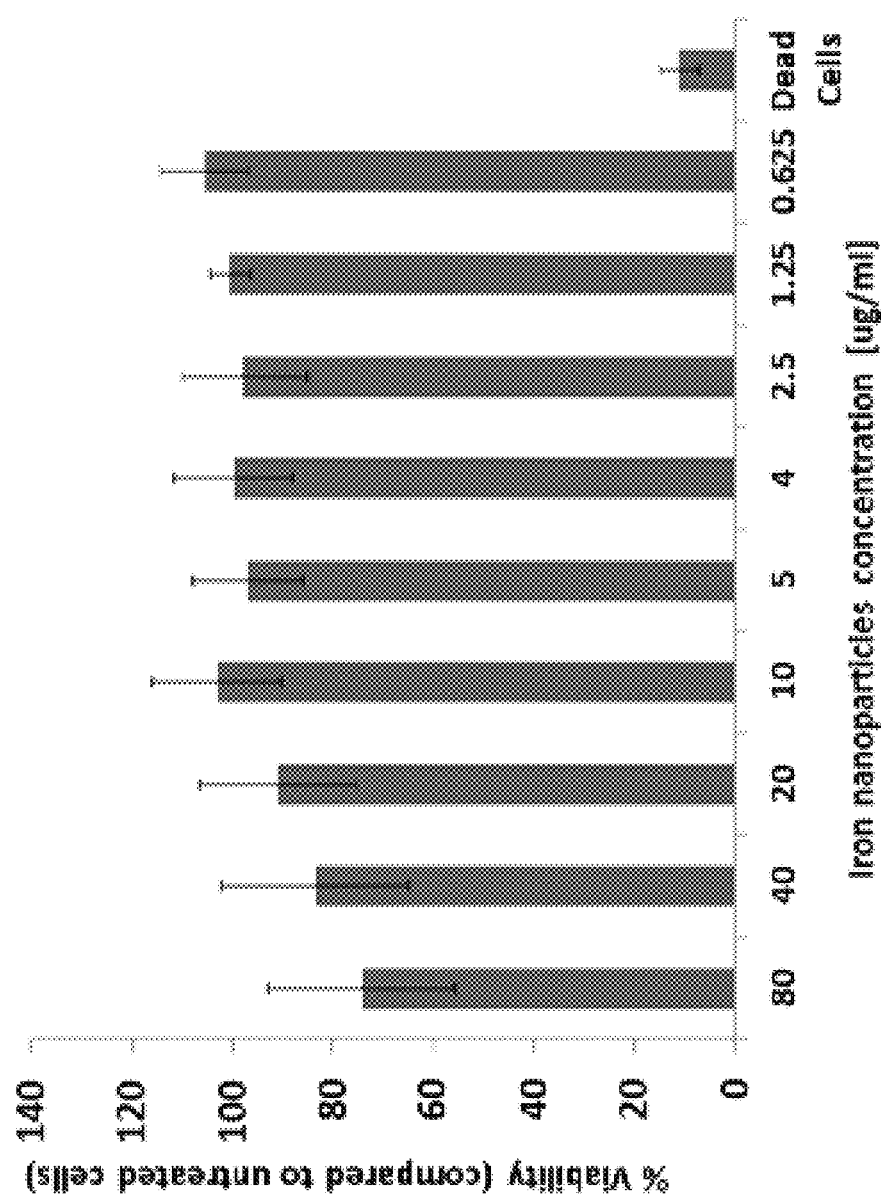
FIG. 9. Cell viability after 3 days of incubation with iron nanoparticles. Percentage of viable RAW 264.7 cells 3 days after the addition of different amounts of iron. Error bars show the standard deviations of the results from 3 repeated experiments.

Cell Viability Experiment: RAW 264.7 cells from ATCC (TIB-71) were cultured in complete DMEM (ATCC® 30-2002™) media (10% FBS, 1% PS). For each experiment 4,000 cells were added to each well and after 24 hr, escalating doses of the carboxyl superparamagnetic nanoparticles were added to each well. Final concentration of nanoparticles ranged from 0.625 [μg iron/ml] to 80 [μg iron/ml]. After 3 days of incubation with the nanoparticles, the media was removed and replaced with 100 μL Cell Lysis Buffer (20 mM Tris, 2 mM EDTA, 150 mM NaCl, 0.5% Triton X-100, pH 7.4). Cells were frozen to ensure complete cell lysis. ATP concentration at the time of lysis was measured using the CellTiter-Glo® Assay. ATP concentration is correlated with metabolic activity in cells. In the CellTiter-Glo® Assay, the CellTiter-Glo® substrate is converted into a luminescent substrate which is proportional to the amount of ATP in the cell lysate. In order to normalize to cell number, the amount of double stranded DNA in the cell lysate was measured by the fluorescence of PicoGreen® reagent. PicoGreen reagent fluoresces upon binding to double stranded DNA. Experimental conditions were normalized to the no treatment control. The viability results are shown in FIG. 9.

5. Modulation Efficiency Measurement

The modulation efficiency of the magnetic guidestar was measured based on the cell samples with magnetic particles. The modulation efficiency is defined as the ratio between the modulated light intensity and the light intensity incident on the guidestar, i.e. the percentage of the light being modulated by the guidestar. To directly measure the modulation efficiency, we removed the scattering sample on the DOPC side of the system as shown in FIGS. 10a-10d and the lens L5 in FIG. 6, to directly image the sample to the camera of the DOPC system. In this case, we can image the field on the guidestar plane by implementing the DOPC recording process for both the field-subtraction method and the frequency-modulation method. To calculate the modulation efficiency, we also measured the reference beam light intensity Ir and the sample beam light intensity Is. For the field-subtraction method, we used the following equation to calculate the modulation efficiency M as described in reference [2].

$$\eta = \frac{|E'_c - E_c|^2}{64 I_s},$$
$$E_c = [(I_0 - I_2) + i(I_1 - I_3)]/\sqrt{I_r}$$
$$E'_c = [(I'_0 - I'_2) + i(I'_1 - I'_3)]/\sqrt{I_r}$$

are the fields reconstructed from the four intensity images Ik (k=1, 2, 3, 4) measured during the 4-phase stepping DOPC recording before and after applying the magnetic field, respectively. FIG. 10b shows the image of $$|E'_c - E_c|/\sqrt{I_r}$$

For the frequency modulation method, we used the equation $$\eta = \frac{|E_c|^2}{16 I_s}, \text{ where}$$
$$E_c = [(I_0 - I_2) + i(I_1 - I_3)]/\sqrt{I_r}$$

is the field reconstructed from the four intensity images Ik (k=1, 2, 3, 4) measured during the 4-phase stepping DOPC recording when the magnetic field is on. FIG. 10c-10e shows the $$|E_c|/\sqrt{I_r}$$

maps where the AC magnetic field has a fundamental frequency of 25 Hz, while the reference beam frequency is set to 25 Hz (c), 50 Hz (d), and 75 Hz (e).

To compute the modulation efficiency from the captured field images, we applied a 10 μm circular region of interest (ROI) to the images of the cells and averaged the amplitude of the field over the top 10% of the pixels within this ROI. Based on Equation S2 and S3, the modulation efficiency using the field-subtraction method is 29%, while that of the frequency-modulation method is 5% (fundamental frequency), 0.5% (second harmonic), and 0.1% (third harmonic).

Thus, as illustrated herein, there are a number of distinct advantages of using magnetic guidestar according to one or more embodiments, compared to ultrasound-based guidestar:

a) The penetration depth of the magnetic field is much larger than ultrasound in some materials such as bone and gas structures. Therefore, the magnetic guidestar (magnetic particle) would be a better candidate compared to ultrasound-related guidestar for applications involving bone or gas bodies.

b) The magnetic guidestar is a non-contact method, while ultrasound requires couplant to transmit ultrasound into the sample.

c) compared to ultrasound alone, the magnetic guidestar has a much higher resolution because the magnetic particle can go down to sub-micron size, while ultrasound focus has a typical size of tens of microns.

Compared to microbubble guidestar, magnetic guidestar is much more stable and thus is able to continuously form a light focus.

Process Steps

Figure 11:
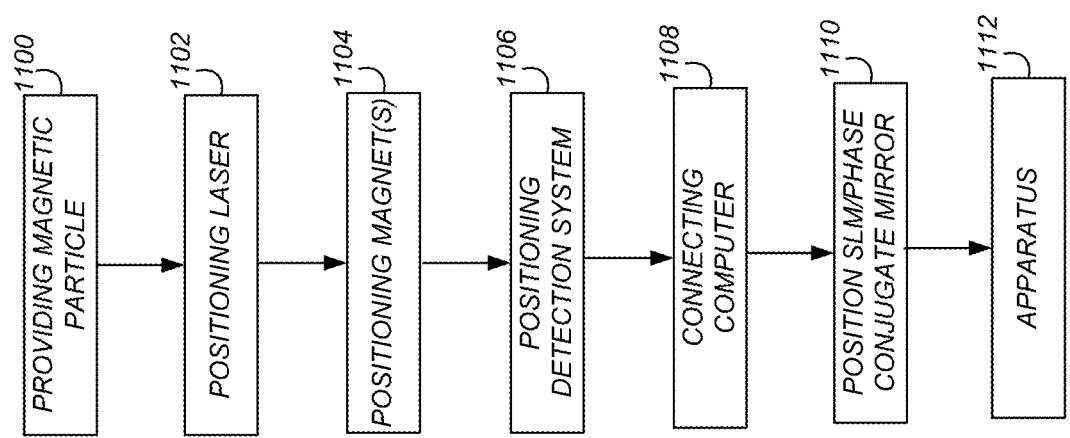
FIG. 11 is a flowchart illustrating a method of making an apparatus according to one or more examples.

FIG. 11 is a flowchart illustrating a method of making an apparatus 100 e.g., for imaging and/or irradiating a target (tagged by a magnetic particle 102) in a scattering medium 124. Examples of scattering media include, but are not limited to, biological tissue.

Block 1100 represent positioning, or obtaining the scattering medium 124 comprising one or more magnetic particles 102, the magnetic particle(s) 102 (e.g., nanoparticle) each having a diameter in a range of (including but not limited to) 2 nanometers to 10 nm, 10 nm-50 nm, 50 nm-100 nm, 100 nm-200 nm, 200 nm-500 nm, 500 nm-1 micrometer, 1-10 micrometers, 10-20 micrometers, 30-40 micrometers, or 40-50 micrometers. Compositions of the magnetic particle 102 include, but are not limited to, any magnetically responsive metal, e.g., but not limited to iron, iron oxide, nickel, cobalt, some alloys of rare-earth metals.

Block 1102 represents optionally positioning a source of input electromagnetic radiation 126, so that the input electromagnetic radiation 126 is incident on/irradiates the magnetic particle 102 in the scattering medium 124 and scatters from the magnetic particle 102 so as to form scattered electromagnetic radiation 112. Example wavelengths of the input electromagnetic radiation include, but are not limited to, wavelengths corresponding to ultraviolet, visible, and infrared electromagnetic radiation. Examples of the source include, but are not limited to, a coherent source such as a laser.

Block 1104 represents providing, obtaining, or positioning one or more magnets 122.

Block 1106 represents optionally positioning a detector/detection system 110, 116 so as to receive the scattered electromagnetic radiation 112, the detector/detection system 110, 116 outputting a recording comprising one or more signals in response the scattered electromagnetic radiation 112 received on the detector 116, 110. In one or more examples, the detector comprises a camera 116 including pixels (e.g., charge coupled device, CCD).

Block 1108 represents optionally connecting a computer or circuit or processor to the detector 116, 110 and/or spatial light modulator (SLM) and/or other modulation device, wherein the computer/circuit/processor determines an output field F2 from the recording of/associated with the scattered electromagnetic radiation 112 received on the detector 110, 116. In one or more examples, the computer/circuit/processor determines a phase and/or amplitude of the output field F2 from the recording.

Block 1110 represents positioning/providing/obtaining a field/wavefront modulation device/modulator comprising a spatial light modulator SLM or phase conjugate mirror, so as to transmit output electromagnetic radiation 130 having the output field F2 (e.g., electric field) determined from the recording of the scattered electromagnetic radiation 112. The scattered electromagnetic radiation 112 comprises a scattered field F formed by scattering from a magnetic particle 102 moving in the scattering medium 124 in response to a magnetic field M applied from the one or more magnets 122. The output electromagnetic radiation 130 forms a focus 128 at the magnetic particle 102 in the scattering medium 124, or at a location/target 120 in the scattering medium tagged by the magnetic particle 102. Further examples of the modulation device include, but are not limited to a digital micromirror device (DMD) or modulator device including pixels whose reflectivity/emissivity is modulated to control the phase and/or amplitude of output electromagnetic radiation (e.g., reference electromagnetic radiation) reflected from or transmitted through the device. In one or more examples, the circuit or computer configures or controls the reflectivity/emissivity of the pixels in the modulator by applying/modulating an electric field applied across liquid crystals between electrodes. The output field F2 is generated when the circuit/computer applies voltages to the electrodes so as to control the magnitude of the output field F2.

Block 1112 represents the end result, an apparatus 100 comprising the one or more magnets 122 configured to apply a magnetic field M to a magnetic particle 102 in a scattering medium 124; and the spatial light modulator SLM or phase conjugate mirror configured to irradiate the scattering medium 124.

The apparatus 100 can be embodied in many ways including, but not limited to the following.

1. The apparatus 100 further comprising the detector 110, 116 outputting the recording including a signal in response to the scattered electromagnetic radiation 112 received on the detector 110, 116.

2. The apparatus 100 of one or any combination of the previous embodiments, including a computer connected to the detector 110, 116 and the spatial light modulator SLM.

3. The apparatus 100 of one or any combination of the previous embodiments, wherein the spatial light modulator SLM modulates the output electromagnetic radiation 130 so that the output electromagnetic radiation 130 has the phase and/or amplitude determined by the computer.

4. The apparatus 100 of one or any combination of the previous embodiments, wherein the computer determines the output field comprising a phase conjugate of the scattered field F of the scattered electromagnetic radiation 112.

5. The apparatus 100 of one or any combination of the previous embodiments, wherein the detector 110, 116 comprises a wavefront sensor measuring the phase and/or amplitude of the scattered field F and the computer determines the phase conjugate of the phase of the scattered field F.

6. The apparatus 100 of one or any combination of the previous embodiments, wherein the one or more signals outputted from detector 110, 116 (in response to receiving the scattered electromagnetic radiation 112) comprise an interference pattern recording interference between the scattered field F and a reference beam 140 (reference electromagnetic radiation) incident on the detector 110, 116.

7. The apparatus 100 of one or any combination of the previous embodiments, wherein the detector 110, 116 comprises a detection system 110 measuring a phase and/or amplitude of the scattered field F using phase shifting holography, and the computer determines the output field F2 from the phase and/or amplitude of the scattered field F.

8. The apparatus 100 of one or any combination of the previous embodiments, wherein the magnetic field M is a time varying magnetic field having a frequency, the scattered field F has the frequency or a harmonic of the frequency, and the output electromagnetic radiation 130 has the frequency or the harmonic of the frequency.

9. The apparatus 100 of one or any combination of embodiments 1-7, wherein the scattered electromagnetic radiation 112 comprises first scattered electromagnetic radiation scattered from the magnetic particle 102 at a first position P1 in the scattering medium 124 and comprising a first scattered field F, and second scattered electromagnetic radiation (comprising a second scattered field F) scattered from the magnetic particle 102 at a second position P2 in the scattering medium 124 after the magnetic particle 102 has moved in response to the magnetic field M. The apparatus 100 further comprises the detector 110, 116 detecting the first scattered field F and the second scattered field F; a circuit or computer connected to the detector 110, 116 determining a difference between the first scattered field F and the second scattered field; and the spatial light modulator SLM forming the output field comprising a phase conjugate of the difference.

10. The apparatus 100 of one or any combination of the previous examples, wherein the magnetic particle 102 has a diameter in a range of 2 nm to 50 micrometers.

11. The apparatus 100 of one or any combination of the previous examples, wherein the magnetic particle 102 comprises iron, iron oxide, cadmium, nickel, or an alloy of a rare-earth metal.

12. The apparatus 100 of one or any combination of previous examples, wherein the magnetic particle 102 comprises a material that interacts with the magnetic field and moves according to a gradient of the magnetic field and/or a magnetically responsive metal.

13. The apparatus 100 of one or any combination of the previous examples, wherein the magnetic particle 102 and the magnetic field M are such that the magnetic particle 102 moves a distance D between 0 nm and 1 millimeter (mm) (e.g., up to 1 mm) in the scattering medium 124 in response to the magnetic field.

14. The apparatus 100 of one or any combination of the previous examples, wherein the magnetic field M has a frequency in a range of 1 Hz-1 MHz.

15. The apparatus 100 of one or any combination of the previous examples, wherein the scattering medium 124 comprises biological tissue 106 including cells mounted on a sample holder coupled to the magnetic field, the detector 110, 116, and the spatial light modulator SLM or phase conjugate mirror.

16. The apparatus 100 of embodiment 15, wherein the in vivo decorrelation time is reduced to at least 50 milliseconds using an immobilization approach.

17. The apparatus 100 of one or any combination of the previous embodiments, wherein the detector 110, 116 has a frame rate of greater than 20 Hz, the spatial light modulator SLM has response rate of greater than 20 Hz, and the input electromagnetic radiation 126 has an intensity up to 200 mW/cm2 (e.g., for tissue safety).

18. The apparatus 100 of one or any combination of the previous embodiments, wherein the phase conjugate mirror comprises a nonlinear optical device (e.g., photorefractive crystal, polymer film).

Example Method of Operation

Figure 12:
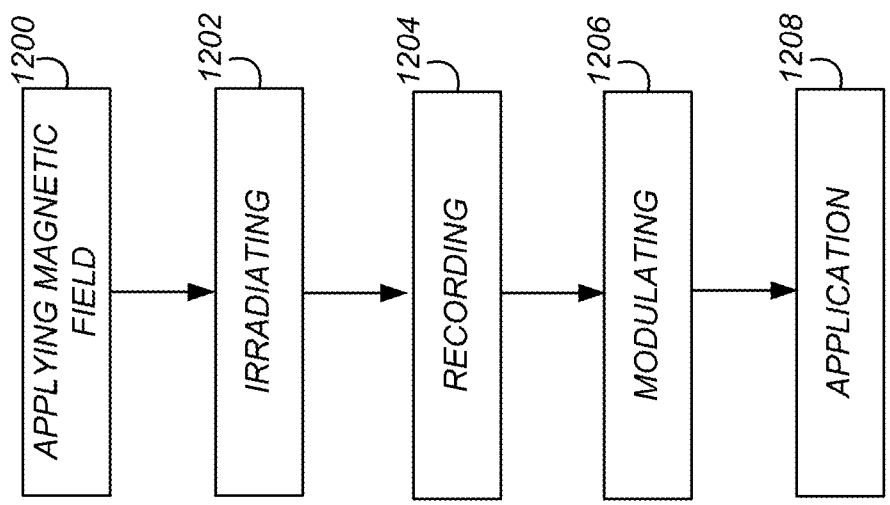
FIG. 12 is a flowchart illustrating a method of operating an apparatus according to one or more examples.

FIG. 12 illustrates a method for irradiating a scattering medium 124.

Block 1200 represents applying a magnetic field to a magnetic particle 102 in a scattering medium 124 so that the magnetic field moves the magnetic particle 102 in the scattering medium 124. Examples of scattering media include, but are not limited to, biological tissue.

Block 1202 represents irradiating the magnetic particle 102 in the scattering medium 124 with electromagnetic radiation 126, wherein the electromagnetic radiation scatters from the magnetic particle 102 so as to form scattered electromagnetic radiation 112.

Block 1204 represents forming a recording of the scattered electromagnetic radiation 112 112 on a detector 110, 116 or a phase conjugate mirror. In one or more examples, the recording comprises an interference pattern recording interference between a reference beam 140 and the scattered electromagnetic radiation 112 on a camera or a phase conjugate mirror. In one or more examples, the step comprises receiving the scattered electromagnetic radiation 112 on a detector 110, 116, wherein the detector 110, 116 outputs the recording comprising one or more signals in response to the scattered electromagnetic radiation 112 received on the detector 110, 116; and determining, in a computer, an output field from the recording.

Block 1206 represents using the recording to modulate output electromagnetic radiation so that the output electromagnetic radiation comprises an output field determined from the recording and forming a focus at the magnetic particle 102 in the scattering medium. In one or more examples, the step comprises modulating the output electromagnetic radiation with the output field using a spatial light modulator.

Block 1208 represents using the modulated output electromagnetic radiation in an application, e.g., to image, diagnose, perform therapy on the scattering medium at the location 120 of the target tagged by the magnetic particle 102.

Processing Environment

Figure 13:
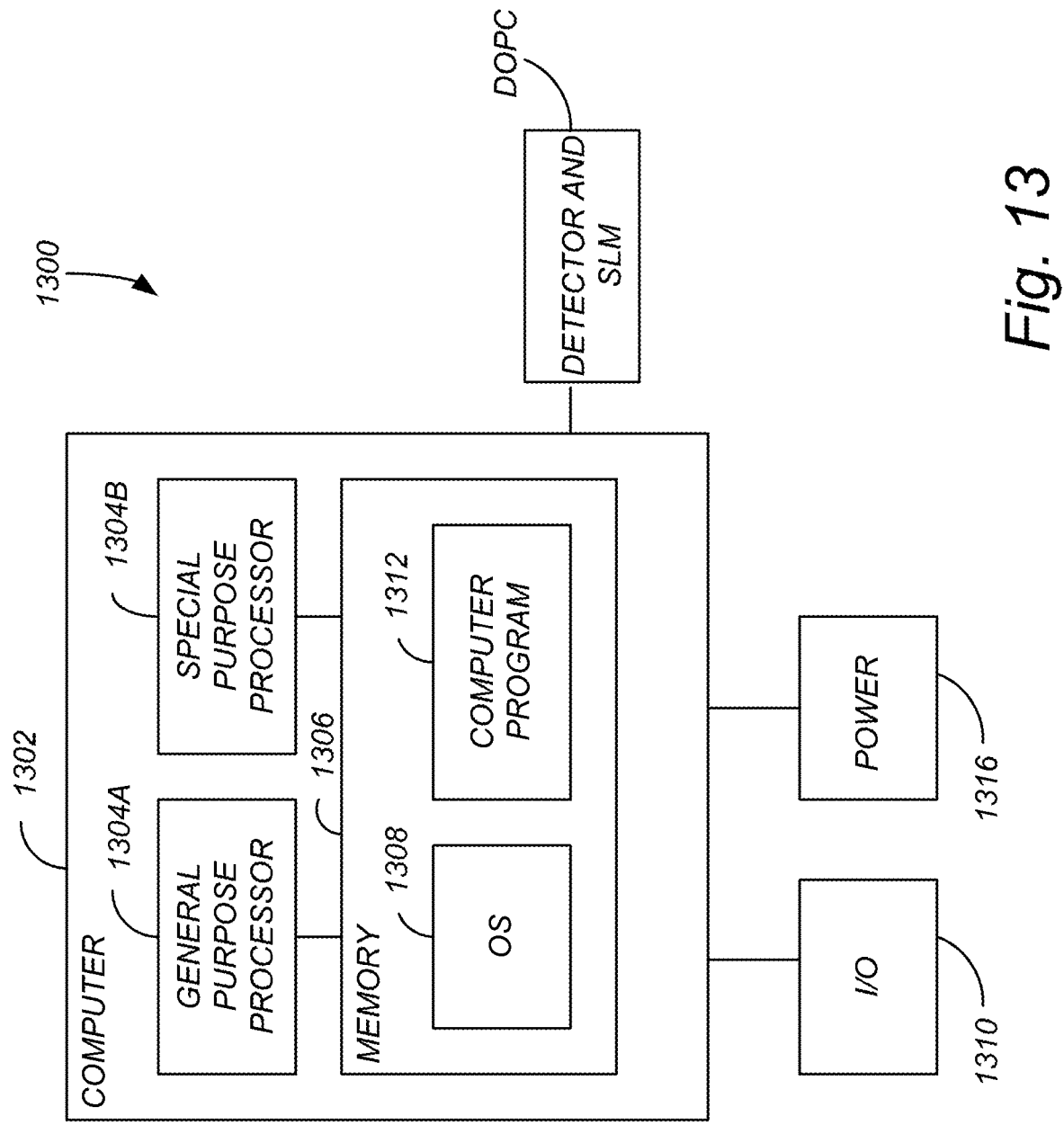
FIG. 13 is a hardware embodiment for implementing the processes described herein, according to one or more examples.

FIG. 13 illustrates an exemplary system 1300 used to implement processing elements needed to measure the scattered field, determine the output field, and/or control the modulator (e.g., SLM) so as to modulate the output electromagnetic radiation with the output field F2.

The computer 1302 comprises a processor 1304 (general purpose processor 1304A and special purpose processor 1304B) and a memory, such as random access memory (RAM) 1306. Generally, the computer 1302 operates under control of an operating system 1308 stored in the memory 1306, and interfaces with the user/other computers to accept inputs and commands (e.g., analog or digital signals from the crew or automatic ice detector) and to present results through an input/output (I/O) module 1310. The computer program application 1312 accesses and manipulates data stored in the memory 1306 of the computer 1302. The operating system 1308 and the computer program 1312 are comprised of instructions which, when read and executed by the computer 1302, cause the computer 1302 to perform the operations and/or methods herein described. In one embodiment, instructions implementing the operating system 1308 and the computer program 1312 are tangibly embodied in the memory 1306, thereby making one or more computer program products or articles of manufacture capable of determining a phase and/or amplitude of the output field from the recording; determining a difference between the first scattered field and the second scattered field; determining the output field comprising a phase conjugate of the scattered field; determining a phase and/or amplitude of the scattered field; determining a phase conjugate of the phase of the scattered field; and/or modulating the pixels on the modulator (SLM) so as to form the output electromagnetic radiation comprising the output (e.g., electric) field. As such, the terms "article of manufacture," "program storage device" and "computer program product" as used herein are intended to encompass a computer program accessible from any computer readable device or media. In one embodiment, the special purpose processor 1304B is an application specific integrated circuit (ASIC). In one or more embodiments, computer 1302 may be coupled to, or may comprise, a personal computer (e.g., desktop computer (e.g., HP Compaq™), portable or media viewing/listening device (e.g., cellular/mobile device/phone, laptop, tablet, personal digital assistant, etc.) or integrated circuit, chip, or field programmable gate array (FPGA). In yet another embodiment, the computer 1302 may comprise a multi-touch device, gaming system, or other internet enabled device executing on various platforms and operating systems.

Those skilled in the art will recognize many modifications may be made to this configuration without departing from the scope of the present disclosure. For example, those skilled in the art will recognize that any combination of the above components, or any number of different components, peripherals, and other devices, may be used.

Advantages and Improvements

We developed and experimentally demonstrated a new guidestar mechanism for optical wavefront shaping, which uses a magnetic field to guide optical focusing inside scattering media. Although the ultrasound guidestar is truly noninvasive and able to target arbitrary positions, it has limited penetration depths due to the strong absorption of high-frequency ultrasound (e.g. 50 MHz). Unfortunately, the use of high-frequencies for ultrasound guidestar is critical; not only because it provides a higher resolution but also because the small focal size reduces the number of optical modes inside the focus, which is inversely proportional to the intensity of the focus [42]. While low-frequency ultrasound (e.g. 1 MHz) with the microbubble guidestar can potentially address this issue, microbubbles are currently limited to the vasculature and not stable for continuous focusing. Moreover, ultrasound of MHz order frequencies is significantly attenuated by bone structures (e.g. skull) and gas bodies (e. g. pulmonary alveoli).

In contrast, magnetic fields have full-body penetration and magnetic particles can be functionalized and enter many locations beyond the vasculature. These features promise to benefit some important biomedical applications such as targeted therapy [43] or neural modulation [44] many millimeters deep in soft tissue and/or through the skull. The magnetic guidestar can also be implanted to a target location for light-based bioelectronics [45]. Interestingly, magnetic particles can be moved within soft tissue by manipulating the external magnetic field [46,47], significantly increasing the flexibility of this method. By combining this ability with a magnetic imaging modality such as MRI or magnetic particle imaging (MPI) [48] to monitor the location of the particles as they are moved by an external field, the position of the magnetic guidestar assisted optical focus can be controlled, thus enabling deep-tissue optical imaging.

The magnetic guidestar has a strong modulation efficiency, since the displacement of magnetic particles can be larger than the wavelength of light. In our experiments, we measured the magnetic particle tagged light using two wavefront measurement methods—the field-subtraction method and the frequency-modulation method. The latter method uses a lock-in scheme to measure the frequency-shifted light from the magnetic particles. While this narrow-band detection method effectively rejects wide-band noise, it also excludes the harmonic signals resulting from the particle oscillation. As a consequence, the modulation efficiency of the frequency-modulation method (5%, see FIG. 10) is lower than that of the field-subtraction method (29%, see FIG. 10) which measures any fluctuation between two measurements. In either case, the modulation efficiency is higher than that of the ultrasound guidestar (1%) [30]. When the magnetic particle is smaller than the size of an optical mode, the modulation efficiency is reduced. Although single nanoparticles are desirable in some applications, these particles commonly accumulate in endosomes into aggregates hundreds of nanometers in size [34], which is on the same scale as optical wavelengths.

Taking advantage of the high modulation efficiency and the small number of optical modes inside the optical focus, the magnetic guidestar enables a PBR of >100, an order of magnitude higher than that of the ultrasound guidestar.

In one or more in vivo applications, the speed of the DOPC process can be improved so that it is faster than the speckle decorrelation time associated with living biological tissue (one millisecond to tens of milliseconds [11,13]). This can be achieved using a faster frame rate of the camera, faster data transfer rate, using an SLM with a faster response, a higher power illumination source to reduce the camera exposure time, and using recently developed high-speed systems [50,51].

Further information on one or more embodiments of the present invention can be found in [52].

REFERENCES

The following references are incorporated by reference herein.
1. V. Ntziachristos, "Going deeper than microscopy: the optical imaging frontier in biology.," Nat. Methods 7, 603-14 (2010).
2. I. M. Vellekoop and A. P. Mosk, "Focusing coherent light through opaque strongly scattering media," Opt. Lett. 32, 2309-2311 (2007).
3. I. M. Vellekoop, "Feedback-based wavefront shaping," Opt. Express 23, 12189-12206 (2015).
4. A. P. Mosk, A. Lagendijk, G. Lerosey, and M. Fink, "Controlling waves in space and time for imaging and focusing in complex media," Nat. Photonics 6, 283-292 (2012).
5. R. Horstmeyer, H. Ruan, and C. Yang, "Guidestar-assisted wavefront-shaping methods for focusing light into biological tissue," Nat. Photonics 9, 563-571 (2015).
6. H. Yu, J. Park, K. Lee, J. Yoon, K. Kim, S. Lee, and Y. Park, "Recent advances in wavefront shaping techniques for biomedical applications," Curr. Appl. Phys. 15, 632-641 (2015).
7. S. M. Popoff, G. Lerosey, R. Carminati, M. Fink, A. C. Boccara, and S. Gigan, "Measuring the Transmission Matrix in Optics: An Approach to the Study and Control of Light Propagation in Disordered Media," Phys. Rev. Lett. 104, 100601 (2010).
8. M. Kim, W. Choi, Y. Choi, C. Yoon, and W. Choi, "Transmission matrix of a scattering medium and its applications in biophotonics," Opt. Express 23, 12648-12668 (2015).
9. T. Chaigne, O. Katz, A. C. Boccara, M. Fink, E. Bossy, and S. Gigan, "Controlling light in scattering media non-invasively using the photoacoustic transmission matrix," Nat. Photonics 8, 58-64 (2013).
10. H. Yu, T. R. Hillman, W. Choi, J. O. Lee, M. S. Feld, R. R. Dasari, and Y. Park, "Measuring Large Optical Transmission Matrices of Disordered Media," Phys. Rev. Lett. 111, 153902 (2013).
11. M. Jang, H. Ruan, I. M. Vellekoop, B. Judkewitz, E. Chung, and C. Yang, "Relation between speckle decorrelation and optical phase conjugation (OPC)-based turbidity suppression through dynamic scattering media: a study on in vivo mouse skin," Biomed. Opt. Express 6, 72-85 (2015).
12. J. Brake, M. Jang, and C. Yang, "Analyzing the relationship between decorrelation time and tissue thickness in acute rat brain slices using multispeckle diffusing wave spectroscopy.," J. Opt. Soc. Am. A 33, 270-5 (2016).
13. Y. Liu, P. Lai, C. Ma, X. Xu, A. A. Grabar, and L. V. Wang, "Optical focusing deep inside dynamic scattering media with near-infrared time-reversed ultrasonically encoded (TRUE) light," Nat. Commun. 6, 5904 (2015).
14. M. Cui and C. Yang, "Implementation of a digital optical phase conjugation system and its application to study the robustness of turbidity suppression by phase conjugation," Opt. Express 18, 3444-3455 (2010).
15. C. Hsieh, Y. Pu, R. Grange, and D. Psaltis, "Digital phase conjugation of second harmonic radiation emitted by nanoparticles in turbid media," Opt. Express 18, 533-537 (2010).
16. I. N. Papadopoulos, S. Farahi, C. Moser, and D. Psaltis, "Focusing and scanning light through a multimode optical fiber using digital phase conjugation.," Opt. Express 20, 10583-90 (2012).
17. T. R. Hillman, T. Yamauchi, W. Choi, R. R. Dasari, M. S. Feld, Y. Park, and Z. Yaqoob, "Digital optical phase conjugation for delivering two-dimensional images through turbid media.," Sci. Rep. 3, 1909 (2013).
18. K. Lee, J. Lee, J.-H. Park, J.-H. Park, and Y. Park, "One-Wave Optical Phase Conjugation Mirror by Actively Coupling Arbitrary Light Fields into a Single-Mode Reflector," Phys. Rev. Lett. 115, 153902 (2015).
19. N. Ji, D. E. Milkie, and E. Betzig, "Adaptive optics via pupil segmentation for high-resolution imaging in biological tissues.," Nat. Methods 7, 141-7 (2010).
20. I. M. Vellekoop and C. M. Aegerter, "Scattered light fluorescence microscopy: imaging through turbid layers.," Opt. Lett. 35, 1245-1247 (2010).
21. F. Kong, R. H. Silverman, L. Liu, P. V Chitnis, K. K. Lee, and Y. C. Chen, "Photoacoustic-guided convergence of light through optically diffusive media.," Opt. Lett. 36, 2053-5 (2011).
22. O. Tzang, E. Niv, A. M. Caravaca-Aguirre, and R. Piestun, "Thermal expansion feedback for wave-front shaping," Opt. Express 25, 6122 (2017).
23. P. Lai, L. Wang, J. W. Tay, and L. V. Wang, "Photoacoustically guided wavefront shaping for enhanced optical focusing in scattering media," Nat. Photonics 9, 126-132 (2015).

24. J. Jang, J. Lim, H. Yu, H. Choi, J. Ha, J.-H. Park, W.-Y. Oh, W. Jang, S. Lee, and Y. Park, "Complex wavefront shaping for optimal depth-selective focusing in optical coherence tomography," Opt. Express 21, 2890 (2013).
25. X. Xu, H. Liu, and L. V Wang, "Time-reversed ultrasonically encoded optical focusing into scattering media," Nat. Photonics 5, 154-157 (2011).
26. Y. M. Wang, B. Judkewitz, C. A. DiMarzio, and C. Yang, "Deep-tissue focal fluorescence imaging with digitally time-reversed ultrasound-encoded light," Nat Commun 3, 928 (2012).
27. K. Si, R. Fiolka, and M. Cui, "Fluorescence imaging beyond the ballistic regime by ultrasound pulse guided digital phase conjugation.," Nat. Photonics 6, 657-661 (2012).
28. H. Ruan, M. Jang, B. Judkewitz, and C. Yang, "Iterative time-reversed ultrasonically encoded light focusing in backscattering mode.," Sci. Rep. 4, 7156 (2014).
29. J. W. Tay, P. Lai, Y. Suzuki, and L. V Wang, "Ultrasonically encoded wavefront shaping for focusing into random media.," Sci. Rep. 4, 3918 (2014).
30. H. Ruan, M. Jang, and C. Yang, "Optical focusing inside scattering media with time-reversed ultrasound microbubble encoded light.," Nat. Commun. 6, 8968 (2015).
31. C. Ma, X. Xu, Y. Liu, and L. V. Wang, "Time-reversed adapted-perturbation (TRAP) optical focusing onto dynamic objects inside scattering media," Nat. Photonics 8, 931-936 (2014).
32. E. H. Zhou, H. Ruan, C. Yang, and B. Judkewitz, "Focusing on moving targets through scattering samples," Optica 1, 227-232 (2014).
33. B. D. Plouffe, S. K. Murthy, and L. H. Lewis, "Fundamentals and application of magnetic particles in cell isolation and enrichment: a review," Reports Prog. Phys. 78, 16601 (2015).
34. E. E. White, A. Pai, Y. Weng, A. K. Suresh, D. Van Haute, T. Pailevanian, D. Alizadeh, A. Hajimiri, B. Badie, and J. M. Berlin, "Functionalized iron oxide nanoparticles for controlling the movement of immune cells.," Nanoscale 7, 7780-9 (2015).
35. C. S. S. R. Kumar and F. Mohammad, "Magnetic nanomaterials for hyperthermia-based therapy and controlled drug delivery," Adv. Drug Deliv. Rev. 63, 789-808 (2011).
36. R. Chen, G. Romero, M. G. Christiansen, A. Mohr, and P. Anikeeva, "Wireless magnetothermal deep brain stimulation.," Science 347, 1477-80 (2015).
37. E. N. Leith and J. Upatnieks, "Holographic Imagery Through Diffusing Media," J. Opt. Soc. Am. 56, 523 (1966).
38. Z. Yaqoob, D. Psaltis, M. S. Feld, and C. Yang, "Optical phase conjugation for turbidity suppression in biological samples," Nat Phot. 2, 110-115 (2008).
39. I. Yamaguchi and T. Zhang, "Phase-shifting digital holography," Opt. Lett. 22, 1268 (1997).
40. A. Schlegel, S. F. Alvarado, and P. Wachter, "Optical properties of magnetite (Fe 3 O 4) Related content Optical properties of magnetite (Fe,O,)," J. Phys. C Solid State Phys. J. Phys 12, (1979).
41. H. Ruan, M. L. Mather, and S. P. Morgan, "Pulsed ultrasound modulated optical tomography with harmonic lock-in holography detection.," J. Opt. Soc. Am. A 30, 1409-16 (2013).
42. I. M. Vellekoop, E. G. van Putten, A. Lagendijk, and A. P. Mosk, "Demixing light paths inside disordered metamaterials," Opt. Express 16, 67 (2008).
43. R. Mooney, L. Roma, D. Zhao, D. Van Haute, E. Garcia, S. U. Kim, A. J. Annala, K. S. Aboody, and J. M. Berlin, "Neural stem cell-mediated intratumoral delivery of gold nanorods improves photothermal therapy.," ACS Nano 8, 12450-60 (2014).
44. H. Ruan, J. Brake, J. E. Robinson, M. Jang, C. Xiao, C. Zhou, V. Gradinaru, and C. Yang, "Optogenetic Control of Neural Activity with Time-Reversed Ultrasound Encoded Light," in Optics in the Life Sciences Congress (OSA, 2017), p. BrM3B.3.
45. K. Birmingham, V. Gradinaru, P. Anikeeva, W. M. Grill, V. Pikov, B. McLaughlin, P. Pasricha, D. Weber, K. Ludwig, and
K. Famm, "Bioelectronic medicines: a research roadmap," Nat. Rev. Drug Discov. 13, 399-400 (2014).
46. S. Kulkarni, B. Ramaswamy, E. Horton, S. Gangapuram, A. Nacev, D. Depireux, M. Shimoji, and B. Shapiro, "Quantifying the motion of magnetic particles in excised tissue: Effect of particle properties and applied magnetic field," J. Magn. Magn. Mater. 393, 243-252 (2015).
47. R. Guduru, P. Liang, J. Hong, A. Rodzinski, A. Hadjikhani, J. Horstmyer, E. Levister, and S. Khizroev, "Magnetoelectric "spin" on stimulating the brain," Nanomedicine 10, 2051-2061 (2015).
48. B. Gleich and J. Weizenecker, "Tomographic imaging using the nonlinear response of magnetic particles," Nature 435, 1214-1217 (2005).
49. M. Jang, H. Ruan, H. Zhou, B. Judkewitz, and C. Yang, "Method for auto-alignment of digital optical phase conjugation systems based on digital propagation.," Opt. Express 22, 14054-71 (2014).
50. D. Wang, E. H. Zhou, J. Brake, H. Ruan, M. Jang, and C. Yang, "Focusing through dynamic tissue with millisecond digital optical phase conjugation," Optica 2, 728-735 (2015).
51. Y. Liu, C. Ma, Y. Shen, J. Shi, and L. V. Wang, "Focusing light inside dynamic scattering media with millisecond digital optical phase conjugation," Optica 4, 280 (2017).
52. Focusing light inside scattering media with magnetic-particle-guided wavefront shaping, by Haowen Ruan et. al., Optica Vol. 4, No. 11, pages 1337-1343 and supporting information, https://doi.org/10.1364/OPTICA.4.001337.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. An apparatus, comprising:
one or more magnets; and
a spatial light modulator or phase conjugate mirror transmitting output electromagnetic radiation having an output field determined from a recording of scattered electromagnetic radiation, wherein:
the scattered electromagnetic radiation comprises a scattered field formed by scattering from a magnetic particle moving in a scattering medium in response to a magnetic field applied from the one or more magnets, and the output electromagnetic radiation forms a focus at
the magnetic particle in the scattering medium.

2. The apparatus of claim 1, further comprising:
a detector outputting the recording including a signal in response to the scattered electromagnetic radiation received on the detector; and
a computer connected to the detector and the spatial light modulator:
the computer determining a phase and/or amplitude of the output field from the recording; and
the spatial light modulator modulating the output electromagnetic radiation so that the output electromagnetic radiation has the phase and/or amplitude.

3. The apparatus of claim 2, wherein:
the computer determines the output field comprising a phase conjugate of the scattered field.

4. The apparatus of claim 3, wherein the detector comprises a wavefront sensor measuring a phase and/or amplitude of the scattered field and the computer determines the phase conjugate of the phase of the scattered field.

5. The apparatus of claim 2, wherein the signal comprises an interference pattern recording interference between the scattered field and a reference beam incident on the detector.

6. The apparatus of claim 2, wherein:
the detector comprises a detection system measuring a phase and/or amplitude of the scattered field using phase shifting holography, and
the computer determines the output field from the phase and/or amplitude of the scattered field.

7. The apparatus of claim 2, wherein:
the magnetic field is a time varying magnetic field having a frequency,
the scattered field has the frequency or a harmonic of the frequency, and
the output electromagnetic radiation has the frequency or the harmonic of the frequency.

8. The apparatus of claim 1, wherein:
the scattered electromagnetic radiation comprises:
first scattered electromagnetic radiation scattered from the magnetic particle at a first position in the scattering medium and comprising a first scattered field, and
second scattered electromagnetic radiation scattered from the magnetic particle at a second position in the scattering medium after the magnetic particle has moved in response to the magnetic field, the second scattered electromagnetic radiation comprising a second scattered field; and
the apparatus further comprises:
a detector detecting the first scattered field and the second scattered field;
a circuit connected to the detector determining a difference between the first scattered field and the second scattered field; and
the spatial light modulator forming the output field comprising a phase conjugate of the difference.

9. The apparatus of claim 1, wherein the magnetic particle has a diameter in a range of 2 nanometers to 50 micrometers.

10. The apparatus of claim 1, wherein the magnetic particle comprises at least one material selected form iron, iron oxide, nickel, cadmium, and an alloy of a rare earth metal.

11. The apparatus of claim 1, wherein the magnetic particle comprises a material that interacts with the magnetic field and moves according to a gradient of the magnetic field.

12. The apparatus of claim 1, wherein the magnetic particle moves a distance up to 1 mm in the scattering medium in response to the magnetic field.

13. The apparatus of claim 1, wherein the magnetic field has a frequency in a range of 1 Hz-1 MHz.

14. The apparatus of claim 1, further comprising:
a source of input electromagnetic radiation, wherein the input electromagnetic radiation incident on the magnetic particle is scattered from the magnetic particle so as to form the scattered electromagnetic radiation;
a detector outputting the recording comprising one or more signals in response the scattered electromagnetic radiation received on the detector;
a computer determining the output field from the recording associated with the scattered electromagnetic radiation received on the detector; and
wherein the spatial light modulator or the phase conjugate mirror modulates the output electromagnetic radiation so that the output electromagnetic radiation comprises the output field and forms a focus at the magnetic particle in the scattering medium.

15. The apparatus of claim 14, wherein the detector has a frame rate of greater than 20 Hz, the spatial light modulator has response rate of greater than 100 kHz, and the input electromagnetic radiation has an intensity up to 200 mW/cm2.

16. The apparatus of claim 1, wherein the scattering medium comprises biological tissue including cells.

17. The apparatus of claim 1, wherein the phase conjugate mirror comprises a nonlinear optical device.

18. A method for irradiating a scattering medium, comprising:
applying a magnetic field to a magnetic particle in a scattering medium so that the magnetic field moves the magnetic particle in the scattering medium;
irradiating the magnetic particle in the scattering medium with electromagnetic radiation, wherein the electromagnetic radiation scatters from the magnetic particle so as to form scattered electromagnetic radiation;
forming a recording of the scattered electromagnetic radiation on a detector or a phase conjugate mirror; and
using the recording to modulate output electromagnetic radiation so that the output electromagnetic radiation comprises an output field determined from the recording and forming a focus at the magnetic particle in the scattering medium.

19. The method of claim 18, wherein the recording comprises an interference pattern recording interference between a reference beam and the scattered electromagnetic radiation on a camera or a phase conjugate mirror.

20. The method of claim 18, further comprising:
receiving the scattered electromagnetic radiation on a detector, wherein the detector outputs the recording comprising one or more signals in response to the scattered electromagnetic radiation received on the detector;
determining, in a computer, an output field from the recording; and
modulating output electromagnetic radiation with the output field using a spatial light modulator.

* * * * *